US006919203B2

(12) United States Patent
Chisari

(10) Patent No.: US 6,919,203 B2
(45) Date of Patent: Jul. 19, 2005

(54) PEPTIDES FOR INDUCING CYTOTOXIC T LYMPHOCYTE RESPONSES TO HEPATITIS B VIRUS

(75) Inventor: Francis V. Chisari, Del Mar, CA (US)

(73) Assignee: The Scripps Research Institute, La Jolla, CA (US)

( * ) Notice: Subject to any disclaimer, the term of this patent is extended or adjusted under 35 U.S.C. 154(b) by 668 days.

(21) Appl. No.: 09/863,054

(22) Filed: May 21, 2001

(65) Prior Publication Data

US 2003/0021809 A1 Jan. 30, 2003

Related U.S. Application Data

(60) Division of application No. 08/463,486, filed on Jun. 5, 1995, now Pat. No. 6,235,288, which is a continuation of application No. 08/396,283, filed on Feb. 27, 1995, now abandoned, which is a division of application No. 08/024,120, filed on Feb. 26, 1993, now abandoned, and a continuation-in-part of application No. 07/935,898, filed on Aug. 26, 1992, now abandoned.

(51) Int. Cl.⁷ .............................................. C12N 15/74
(52) U.S. Cl. ................... 435/320.1; 514/44; 424/189.1; 424/227.1; 530/327; 530/328
(58) Field of Search .......................... 435/320.1, 320.5; 424/189.1, 227.1; 530/327, 328; 514/44

(56) References Cited

U.S. PATENT DOCUMENTS

| | | | |
|---|---|---|---|
| 3,645,852 A | 2/1972 | Axen et al. | |
| 4,235,877 A | 11/1980 | Fullerton | |
| 4,428,941 A | 1/1984 | Galibert et al. | |
| 4,487,715 A | 12/1984 | Nitecki et al. | |
| 4,599,230 A | 7/1986 | Milich et al. | |
| 4,599,231 A | 7/1986 | Milich et al. | |
| 4,659,569 A | 4/1987 | Mitsuhashi et al. | |
| 4,818,527 A | 4/1989 | Thornton et al. | |
| 4,882,145 A | 11/1989 | Thornton et al. | |
| 4,935,235 A | 6/1990 | Rutter et al. | |
| 5,017,558 A | 5/1991 | Vyas | |
| 5,019,386 A | 5/1991 | Machida et al. | |
| 5,039,522 A | 8/1991 | Neurath | |
| 5,100,662 A | 3/1992 | Bolcsak et al. | |
| 5,133,961 A | 7/1992 | Ellis et al. | |
| 5,143,726 A | 9/1992 | Thornton et al. | |
| 5,158,769 A | 10/1992 | Neurath et al. | |
| 5,780,036 A | 7/1998 | Chisari | |
| 5,788,969 A | 8/1998 | Chisari | |
| 5,840,303 A | 11/1998 | Chisari et al. | |
| 5,932,224 A | 8/1999 | Chisari | |
| 6,322,789 B1 | 11/2001 | Vitiello et al. | |
| 6,607,727 B1 | 8/2003 | Chisari et al. | |
| 2003/0171538 A1 | 9/2003 | Chisari | |

FOREIGN PATENT DOCUMENTS

| | | |
|---|---|---|
| EP | 013 828 A1 | 8/1980 |
| EP | 105 481 A1 | 4/1984 |
| EP | 271 302 A2 | 12/1987 |
| EP | 293 201 A1 | 11/1988 |
| EP | 326 111 A2 | 1/1989 |
| EP | 327369 A2 | 8/1989 |
| EP | 431 327 B1 | 6/1991 |
| EP | 469 281 A1 | 2/1992 |
| EP | 534 615 A2 | 3/1993 |
| GB | 2034323 | 6/1980 |
| JP | 161999 * | 8/1985 |
| JP | 64-025800 | 1/1989 |
| WO | WO 92/00753 A1 | 1/1992 |
| WO | WO 93/03753 A1 | 3/1993 |
| WO | WO 94/03205 A1 | 2/1994 |
| WO | WO 94/20127 A1 | 9/1994 |
| WO | WO 94/25060 A1 | 11/1994 |
| WO | WO 95/03777 A1 | 2/1995 |
| WO | WO 95/04817 A1 | 2/1995 |

OTHER PUBLICATIONS

Deres et al., In vivo priming of virus specific cytotoxic T lymphocytes with synthetic lipopeptide vaccine. Nature, Nov. 30, 1989, 342:561–564.*

Rotzschke et al., Isolation and analysis of naturally processed viral peptides as recognized by cytotoxic T cells. Nature, Nov. 15, 1990, 348:252–254.*

Bertoletti et al., HLA class I–restricted human cytotoxic T cells recognize endogenously synthesized hepatitis B nucleocapsid antigen PNAS USA, Dec. 1991, 88:10445–10449.*

Penna et al., Hepatitis B virus (HBV) specific cytotoxic T cell (CTL) response in humans: Characterization of HLA calss II–restricted CTLs that recognize endogenously synthesized HBV envelope antigens. J. Virol., Feb. 1992, 66:1193–1198.*

Bertoletti, A. et al. "Definition of a minimal optimal cytotoxic T–cell epitope within the hepatitis B virus nucleocapsid protein," *Virology*, 1993, 67(4):2376–2380.

Carbone, F.R. and M.J. Bevan "Induction of Ovalbumin–Specific Cytotoxic T Cells by In Vivo Peptide Immunization" *J. Exp. Med.*, Mar. 1989, 169:603–612.

Collins, D.S. et al. "Processing of Exogenous Liposome–Encapsulated Antigens In Vivo Generates Class I MHC–Restricted T Cell Response" *J. Immunology*, 1992, 148:3336–3341.

Lee, K.K. et al. "Cross–Reactive and Strain–Specific Antipeptide Antibodies to *Pseudomonas aeruginosa* PAK and PAO Pili" *Infection and Immunity*, Sep. 1990, 58(9):2727–2732.

(Continued)

Primary Examiner—Donna C. Wortman
(74) Attorney, Agent, or Firm—Saliwanchik, Lloyd & Saliwanchik

(57) ABSTRACT

Peptides are used to define epitopes that stimulate HLA-restricted cytotoxic T lymphocyte activity against hepatitis B virus antigens. The peptides are derived from regions of HBV envelope, and are particularly useful in treating or preventing HBV infection, including methods for stimulating the immune response of chronically infected individuals to respond to HBV antigens.

12 Claims, 6 Drawing Sheets

OTHER PUBLICATIONS

Mack, D.H. et al. "Hepatitis B Virus Particles Contain a Polypeptide Encoded by the Largest Open Reading Frame: A Putative Reverse Transcriptase" *J. Virology*, Dec. 1988, 62(12):4786–4790.

Pasek, M. et al. "Hepatitis B virus genes and their expression in *E. coli*" *Nature*, Dec. 6, 1979, 282:575–579.

Reddy, R. et al. "In Vivo Cytotoxic T Lymphocyte Induction with Soluble Proteins Administered in Liposomes" *J. Immunology*, Mar. 1, 1992, 148(5):1585–1589.

Yssel, H. et al. "T Cell Activation–Inducing Epitopes of the House Dust Mite Allergen *Der p I*" *J. Immunology*, Feb. 1, 1992, 148(3):738–745.

Bertoletti, A. et al. "Natural variants of cytotoxic epitopes are T–cell receptor antagonists for antiviral cytotoxic T cells" *Nature*, Jun. 2, 1994, 369:407–410.

Bichko et al. "Subtype ayw variant of hepatitis B virus" *FEBS Lett.*, 1985, 185:208–212.

Bowie et al. "Deciphering the Message In Protein Sequences: Tolerance to Amino Acid Substitutions" *Science*, 1990, 247:1306–1310.

Carbone et al. "Induction of Cytotoxic T Cells by Primary in vitro Stimulation with Peptides" *J. Exp. Med.*, 1988, 167:1767–1779.

De Magistris, M.T. et al. "Antigen Analog–major histocompatibility complexes act as antagonists of the T cell receptor" *Cell*, Feb. 21, 1992, 68(4):625–634.

Falk et al. "Allele–specific motifs revealed by sequencing of self–peptides eluted from MHC molecules" *Nature*, May 1991, 351:290–296.

Galibert et al. "Nucleotide sequence of the hepatitis B virus genome (subtype ayw) cloned in *E. coli*" *Nature*, 1979, 281:646–650.

Hilleman "Comparative Biology and Pathogenesis of AIDS and Hepatitis B Viruses: Related but Different" *AIDS Res. Hum. Retrovir.*, 10:1409–1419.

Jameson, S.C. et al. "Clone–specific T cell receptor antagonists of major histocompatibility complex class I–restricted cytotoxic T cells" *J. Exp. Med.*, Jun. 1, 1993, 177(6):1541–1550.

Kumar et al. "Amino acid variations at a single residue in an autoimmune peptide profoundly affect its properties" *PNAS USA*, 1990, 87:1337–1341.

Lewin "When Does Homology Mean Something Else?" *Science*, 1987, 237:1570.

Milich et al. "Immune Response to Hepatitis B Virus Core Antigen (HBcAg): Localization of T Cell Recognition Sites Within HBcAg/HBeAg" *J. Immunol.*, 1987, 139:1223–1231.

Nayersina et al. "HLA A2 Restricted Cytotoxic T Lymphocyte Responses to Multiple Hepatitis B Surface Antigen Epitopes during Hepatitis B Virus Infection" *J. Immunol.*, 1991, 150:4659–4671.

Reeck et al. "Homology in Proteins and Nucleic Acids: A Terminology Muddle and a Way out It" *Cell*, 1987, 50:667.

Ruppert, J. et al. "Prominent role of secondary anchor residues in peptide binding to HLA–A2.1 molecules" *Cell*, 1993, 74(5):929–937.

Tong et al. "Active Hepatitis B Virus Replication in the Presence of Anti–HBe is Associated with Viral Variants Containing on Inactive Pre–C Region" *Virology*, 1990, 176:596–603.

Vitiello, A et al. "Development of a lipopeptide–based therapeutic vaccine to treat chronic HBV Infection. I. Induction of a primary cytotoxic T lymphocyte response in humans" *J. of Clin. Invest.*, Jan. 1995, 95(1):341–349.

Greenstein, J.L. et al. "A universal T cell epitope–containing peptide from hepatitis B surface antigen can enhance antibody specific for HIV gp120" *J. Immunology*, 1992, 148:3970–3977.

Watari, E. et al. "A synthetic peptide induces long–term protection from lethal infection with herpes simplex virus 2" *J. Exp. Med.*, 1987, 165(2):459–470.

Hopp, T.P. "Immunogenicity of a synthetic HBsAg peptide: enhancement by conjugation to a fatty acid carrier" *Mol. Immunol.*, 1984, 21(1):13–16.

Bessler, W.G. et al. "The synthetic analog of bacterial lipoprotein are potent immunoadjuvants in combination with or covalently linked to antigen" *Prog. Leukocyte Biol.*, 1986, 5:337–344.

Parker et al. "Peptide Binding to HLA–A2 and HLA–B27 Isolated from *E. coli*" *J. Biol. Chem.*, 1992, 267:5451–5459.

Penna et al. "Cytotoxic T Lymphocytes Recognize an HLA–A2–restricted Epitope within the Hepatitis B Virus Nucleocapsid Antigen" *Exp. Med.*, 1991, 174:1565–1570.

Ferrari et al. "Identification of Immunodominant T Cell Epitopes of the Hepatitis B Virus Nucleocapsid Antigen" *J. Clin. Invest.*, 1991, 88:214–222.

Roitt et al. "Immunology", $3^{rd}$ Ed., Mosby, St. Louis, p. 4.14, 1993.

Zinkernagel et al. "The Lymphoreticular System In Triggering Virus Plus Self–Specific Cytotoxic T Cells: Evidence for T Help" *J. Exp. Med.*, 1978, 147:897–911.

Von Boehmer et al. "Distinct Ir Genes for Helper and Killer Cells in the Cytotoxic Response to H–Y Antigen" *J. Exp. Med.*, Nov. 1979, 150:1134–1142.

Melief et al. "Cooperation Between Subclasses of T Lymphocytes in the in vitro Generation of Cytotoxicity Against a Mutant H–2K Difference an Analysis with Anti–LytAntisera" *Eur. J. Immunol*, 1979, 9:7–12.

Widmer et al. "Antigen–derived helper cell–independent cloned cytolytic T lymphocytes" *Nature*, 1981, 294:750–752.

Lerner et al. "Chemically synthesized peptides predicted form the nucleotide sequence of the hepatitis B virus genome elicit antibodies reactive with the native envelope protein of Dane particles" *Proc. Natl. Acad. Sci. USA*, Jun. 1981, 78:3403–3407.

Bhatnagar et al. "Immune response to synthetic peptide analogues of hepatitis B surface antigen specific for the determinant" *PNAS USA*, Jul. 1982, 79:4400–4404.

Mondelli et al. "Specificity of T lymphocyte cytotoxicity to autologous hepatocytes in chronic hepatitis B virus infection: evidence that T cells are directed against HBV core antigen expressed on hepatocytes" *J. Immunol.*, Dec. 1982, 129:2773–2778.

Von Boehmer et al. "Autonomously proliferating K/D–restricted cytolytic T cell clones" *Eur. Immunol.*, 1983, 12:176–179.

Neurath et al. "Specificity of antibodies elicited by a synthetic peptide having a sequence in common with a fragment of a virus protein—The hepatitis B surface antigen" *Develop. Biol. Standard*, 1983, 54:103–112.

Von Boehmer et al. "Lyt–2 T cell–independent functions of Lyt–2+ cells stimulated with antigen or concanavalin A" *J. Immunol.*, Jul. 1984, 133:59–64.

Milich et al. "Immunogenetics and cellular correlates of the immune response to hepatitis B surface antigen determinants" *Adv. Hepatitis Res.*, Masson, N.Y., N.Y. Usa 91–109, 1984.

Fujii et al. "Peptide Chemistry 1983" published 1984 by Protein Research Foundation (OSAKA), pp. 215–220.

Sprent et al. "Properties of purified T cell subsets" *J. Exp. Med.*, Dec. 1985, 162:2068–2088.

Townsend et al. "The epitope of influenza nucleoprotein recognized by cytotoxic T lymphocytes can be defined with short synthetic peptides" *Cell*, Mar. 28, 1986, 44:959–968.

Gotch et al. "Cytotoxic T lymphocytes recognize a fragment of influenza virus matrix protein in associate with HLA–A2" *Nature*, Apr. 30, 1987, 326:881–882.

Buller et al. "Induction of cytotoxic T–cell responses in vivo in absence of CD4 helper cells" *Nature*, Jul. 2, 1987, 328:76–79.

Milich et al. "Antibody production to the nucleocapsid and envelope of the hepatitis B virus primed by a single synthetic T cell site" *Nature*, Oct. 9, 1987, 329:547–549.

Mondelli et al. "Definition of hepatitis B virus (HBV)–specific target antigens recognized by cytotoxic T cells in acute HBV infection" *Clin. Exp. Immunol.*, 1987, 68:242–250.

Milich et al. "Hepatitis B synthetic immunogen comprised of nucleocapsid T–cell sites and an envelope B–cell epitope" *PNAS USA*, Mar. 1988, 85:1610–1614.

Celis et al. "Recognition of hepatitis B surface antigen by human T lymphocytes" *J. Immunol.*, Mar. 15, 1988, 140:1808–1815.

Moore et al. "Introduction of soluble protein into the Class I pathway of antigen processing and presentation" *Cell*, Sep. 9, 1988, 54:777–785.

Milich et al. "Comparative Immunogenicity of Hepatitis B virus core and E antigens" *J. Immunol.*, Nov. 15, 1988, 141:3617–3624.

Gotch et al. "Recognition of influenza A matrix protein by HLA–A2–restricted cytotoxic T lymphocytes" *J. Exp. Med.*, Dec. 1988, 163:2045–2057.

Milich "T– and B–cell recognition of hepatitis B viral antigens" *Immunol. Today*, 1988, 9:380–386.

Hayashi et al. "Studies on peptides CLXVI. Solid–phase synthesis and immunological properties of fragment peptides related to human hepatitis B virus surface antigen (HBsAg) and its pre–S2 gene" *Chem. Pharm. Bull.*, 1988, 36(12):4993–4994.

Braciale et al. "Class I major histocompatibility complex–restricted cytolytic T lymphocytes recognize a limited number of sites on the influenza hemagglutinin" *PMAS USA*, Jan. 1989, 86:277–281.

Klavinskis et al. "Molecularly engineered vaccine which expresses an immunodominant T–cell epitope induces cytotoxic T lymphocytes that confer protection for lethal virus infection" *J. Virol.*, Oct. 1989, 63:4311–4316.

Bevan "Stimulating killer cells" *Nature*, Nov. 30, 1989, 342:478–479.

Tam et al. "Vaccine engineering" Enhancement of immunogenicity of synthetic peptide vaccines related to hepatitis in chemically defined models consisting of T– and B–cell epitopes *PNAS USA*, Dec. 1989, 86:9084–9088.

Chisari et al. "Hepatitis B virus structure and biology" *Microbial Pathogenesis*, 1989, 6:311–325.

Moriyama et al. "Immunobiology and pathogenesis of hepatocellular injury in hepatitis B virus transgenic mice" *Science*, Apr. 20, 1990, 248:361–364.

Aichele et al. "Antiviral cytotoxic T cell response induced by in vivo priming with a free synthetic peptide" *J. Exp. Med.*, May 1990, 171:1815–1820.

Aggarwal et al. "Oral Salmonella: Malaria Circumsporozolte recombinants induce specific $CD8^+$cytotoxic T cells" *J. Exp. Med.*, Oct. 1990, 172:1083–1090.

Van Bleek et al. "Isolation of an endogenously processed immunodominant viral peptide from the class $IH-2K^B$ molecule" *Nature*, Nov. 15, 1990, 348:213–216.

Golvano et al. "Polarity of Immunogens: implications for vaccine design" *Eur. J. Immunol.*, 1990, 20:2363–2366.

Ishioka et al. "Class I MHC–restricted, peptide–specific cytotoxic T lymphocytes generated by peptide priming in vivo" *Vaccines 90*, Cold Spring Harbor Press, p. 7–11, 1990.

Kast et al. "Protection against lethal Sendai virus infection by in vivo priming of virus–specific cytotoxic T lymphocytes with a free synthetic peptide" *PNAS USA*, Mar. 1991, 88:2283–2287.

Schumacher et al. "Peptide selection by MHC class I molecules" *Nature*, Apr. 25, 1991, 350:703–706.

Sarobe et al. "Induction of antibodies against peptide Hapten does not require covalent linkage betweeen Hapten & class II presentable T helper peptide" *Eur. J. Immunol.*, 1991, 21:1555–1558.

Cassell et al. "Linked recognition of helper and cytotoxic antigenic determinants for the generation f cytotoxic T lymphocytes" *Ann. N.Y. Acad. Sci.*, 1991, pp. 51–60.

Guilhot et al. "Hepatitis B virus (HBV)–specific cytotoxic T–cell response in humans: Production of target cells by stable expression of HBV–encoded proteins in immortalized human B–cell lines" *J. Virol.*, May 1992, 66:2670–2678.

Wakita et al. "Gamma–interferon production response to hepatitis B core protein & synthetic peptides in patients with chronic hepatitis B virus infection" *Digestion*, 1990, 47:149–155.

\* cited by examiner

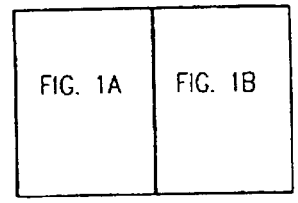
FIG. 1
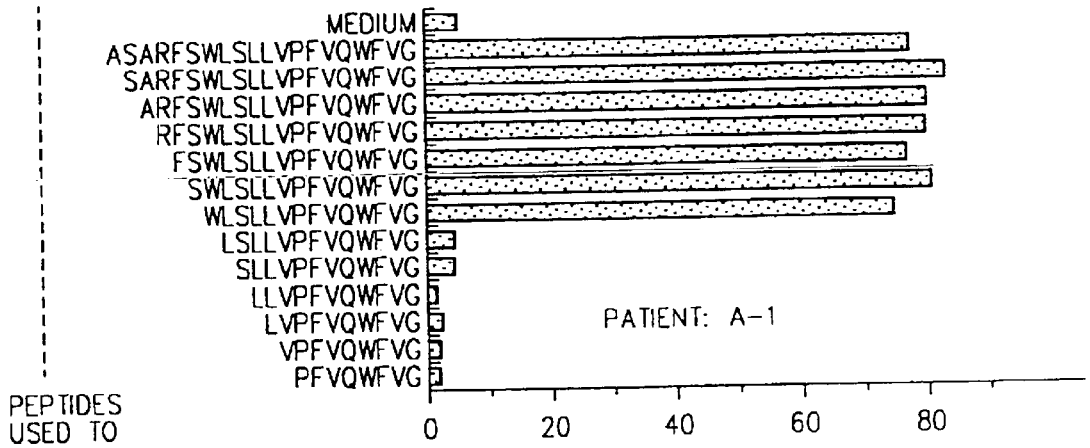
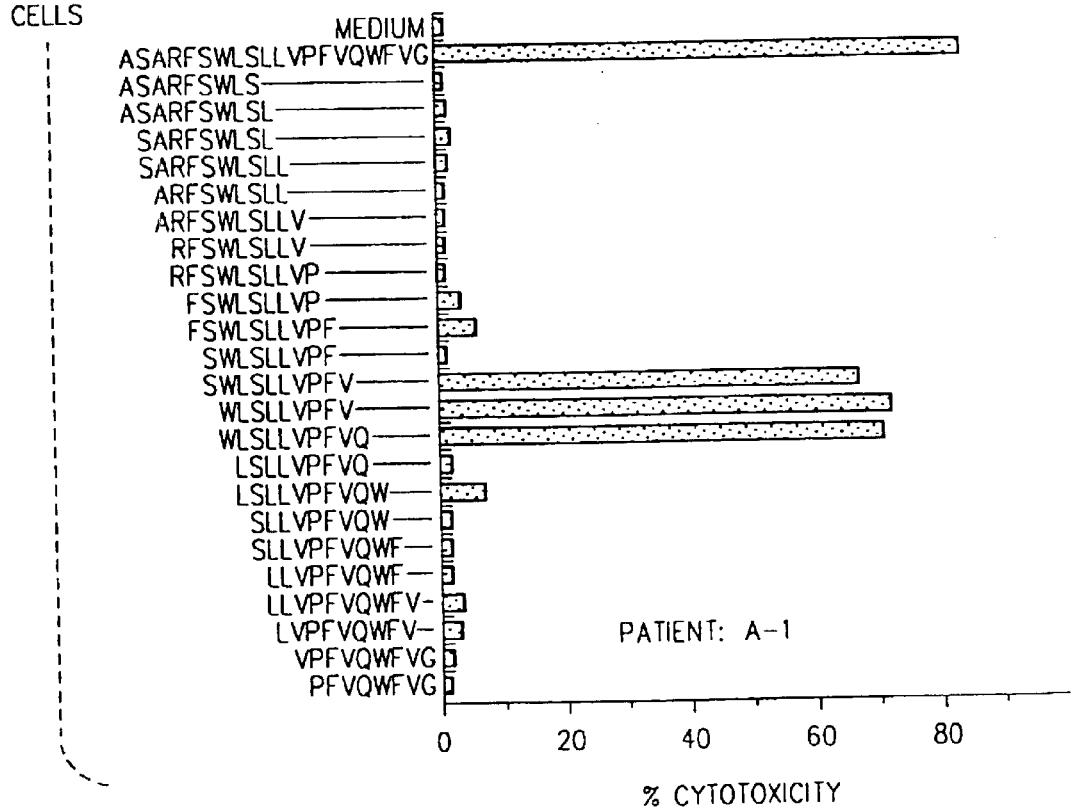

PATIENT: A-3

PATIENT: A-3

% CYTOTOXICITY

PEPTIDES FOR INDUCING CYTOTOXIC T LYMPHOCYTE RESPONSES TO HEPATITIS B VIRUS

RELATED APPLICATION

The present application is a divisional of U.S. application Ser. No. 08/463,486 filed Jun. 5, 1995; U.S. Pat. No. 6,235,288 which is a continuation of application Ser. No. 08/396,283, filed Feb. 27, 1995, now abandoned, which is a continuation of U.S. Ser. No. 08/024,120, filed Feb. 26, 1993, abandoned and is a continuation-in-part of U.S. application Ser. No. 07/935,898, filed Aug. 26, 1992 and now abandoned. Each application is herein incorporated by reference.

GOVERNMENT SUPPORT

This invention was made with government support under Contract No. AI 20001 by the National Institutes of Health. The government has certain rights in this invention.

BACKGROUND OF THE INVENTION

Cytotoxic T lymphocytes (CTLs) play an essential role in fighting cells infected with viruses, intracellular bacteria and parasites, and tumor cells. They do so by direct cytotoxicity and by providing specific and nonspecific help to other immunocytes such as macrophages, B cells, and other T cells. Infected cells or tumor cells process antigen through intracellular events involving proteases. The processed antigen is presented on the cellular surface in the form of peptides bound to HLA class I molecules to T cell receptors on CTLs. MHC class I molecules can also bind exogenous peptides and present them to CTLs without intracellular processing.

At the present time it is difficult to accurately predict from the sequence of an antigenic protein how the protein will be processed and which peptide portions will bind HLA class I molecules and be presented to CTLs. Binding motifs have been predicted for some HLA class I molecules based on sequence analysis of peptides eluted from these molecules (Falk et al., *Nature* 351:290 (1991)). Further, of the peptides that are processed and do bind to HLA class I, which ones will contain CTL-recognizable epitopes is not yet predictable.

Hepatitis B Virus ("HBV") is a non-lytic virus which has currently infected approximately 250 million people worldwide. HBV infection in adults typically leads to an acute disease in the majority of cases, and to a chronic disease state in a minority of patients. This ratio of acute to chronic is reversed when the infection occurs close to the time of birth. There is an increased incidence of hepatocellular carcinoma in chronic HBV infection. A small percentage of individuals who are infected with HBV in adulthood develop fulminant hepatitis associated with a strong immune response with high lethality.

While there is no effective treatment for HBV infection, vaccines have been developed in recent years to prevent HBV infection. The vaccines employ either HBV surface antigen (HBsAg) purified from the plasma of chronic HBV carriers, or HBsAg produced by recombinant DNA technology. Synthetic HBsAg peptide-based vaccines have also been proposed. See, for example, U.S. Pat. Nos. 4,599,230 and 4,599,231. The anti-HBsAg vaccines, however, afford protection in only about 90% of immunized individuals. Those who are unimmunized, or immunized but unprotected, provide a significant reservoir of potential infection.

The contribution of CTLs to immunity to HBV antigens has been difficult to assess. Chisari et al. (*Microbial Pathogen.* 6:31 (1989)) have suggested that liver cell injury may be mediated by an HLA-Class I restricted, $CD8^+$ cytotoxic T cell response to HBV encoded antigens. Class I major histocompatibility (MHC)-restricted cytotoxic T lymphocyte responses have been identified for a variety of other viruses, such as influenza. For example, Townsend et al., *Cell* 44:959 (1986) reported that epitopes of an influenza virus nucleoprotein recognized by cytotoxic T lymphocytes could be defined by synthetic peptides. In attempting to define the cytotoxic T lymphocyte response to HBV, it has been shown that peripheral blood lymphocytes from patients with acute and chronic HBV may be able to kill autologous hepatocytes in vitro, but the specificity of the cytolytic activity, its HLA restriction elements, and cellular phenotype were not established. See, Mondelli et al., *J. Immunol.* 129:2773 (1982) and Mondelli et al., *Clin. Exp. Immunol.* 6:311 (1987). Moriyama et al., *Science* 248:361–364 (1990), have reported that the HBV major envelope antigen is expressed at the hepatocyte surface in a form recognizable by envelope-specific antibodies and by MHC class I-restricted, $CD8^+$ cytotoxic T lymphocytes.

As there is a large reservoir of individuals chronically infected with HBV, it would be desirable to stimulate the immune response of these individuals to respond to appropriate HBV antigens and thereby eliminate their infection. It would also be desirable to prevent the evolution to a chronic HBV infection in individuals suffering from an acute phase infection. Further, as the presently approved HBV vaccines do not elicit protective immunity in about 10% of immunized individuals, it would be desirable to elicit more effective immunity, such as by increasing or diversifying the immunogenicity of the vaccines. Quite surprisingly, the present invention fulfills these and other related needs.

SUMMARY OF THE INVENTION

The present invention provides peptides which induce MHC class I restricted cytotoxic T lymphocyte responses against HBV antigen. The peptides of interest are derived from the HBV envelope. In certain embodiments the CTL inducing peptide will have the sequence HBenv183-191 Phe-Leu-Thr-Arg-Ile-Leu-Thr-Ile (Seq. ID No. 1); HBenv248-257 Phe-Ile-Leu-Leu-Leu-Cys-Leu-Ile-Phe-Leu (Seq. ID No. 3); HBenv249-257 Ile-Leu-Leu-Leu-Cys-Leu-Ile-Phe-Leu (Seq. ID No. 4); HBenv249-258 Ile-Leu-Leu-Leu-Cys-Leu-Ile-Phe-Leu-Leu (Seq. ID No. 5); HBenv250-258 Leu-Leu-Leu-Cys-Leu-Ile-Phe-Leu-Leu (Seq. ID No. 6); HBenv251-259 Leu-Leu-Cys-Leu-Ile-Phe-Leu-Leu-Val (Seq. ID No. 7), HBenv251-260 Leu-Leu-Cys-Leu-Ile-Phe-Leu-Leu-Val-Leu (Seq. ID No. 8), HBenv260-269 Leu-Leu-Asp-Tyr-Gln-Gly-Met-Leu-Pro-Val (Seq. ID No. 9), HBenv335-343 Trp-Leu-Ser-Leu-Leu-Val-Pro-Phe-Val (Seq. ID No. 10), HBenv152-161 Ser-Ile-Leu-Ser-Lys-Thr-Gly-Asp-Pro-Val (Seq. ID No. 11); HBenv177-185 Val-Leu-Gln-Ala-Gly-Phe-Phe-Leu-Leu (Seq. ID No. 12); HBenv204-212 Phe-Leu-Gly-Gly-Thr-Pro-Val-Cys-Leu (Seq. ID No. 13); or HBenv370-379 Ser-Ile-Val-Ser-Pro-Phe-Ile-Pro-Leu-Leu (Seq. ID No. 14); or will have a sequence substantially homologous to one of the foregoing sequences. The peptide can be optionally flanked and/or modified at one or both of the N- and C-termini, as desired. Conservative substitutions, deletions and additions may be made at non-critical residue positions within the selected peptide without substantially adversely affecting its biological activity.

In the various peptide embodiments it will be understood that the peptides can be polymerized, each to itself to form larger homopolymers, or with different peptides to form heteropolymers. In some instances peptides will be combined in a composition as an admixture and will not be linked. The peptide can also be conjugated to a lipid-containing molecules capable of enhancing a T lymphocyte response, or to a different peptide which induces a T-helper cell response, for example.

Compositions are provided which comprise a peptide of the invention formulated with an additional peptide, a liposome, an adjuvant and/or a pharmaceutically acceptable carrier. Thus, pharmaceutical compositions can be used in methods of treating acute HBV infection, particularly in an effort to prevent the infection from progressing to a chronic or carrier state. Methods for treating chronic HBV infection and HBV carrier states are also provided, where the pharmaceutical compositions are administered to infected individuals in amounts sufficient to stimulate immunogenically effective cytotoxic T cell responses against HBc epitopes. For treating these infections it may be particularly desirable to combine the peptides which induce MHC class I restricted cytotoxic T lymphocyte responses against HBV antigen with other peptides or proteins that induce immune response to other HBV antigens, such as HBV core. To treat individuals with chronic or carrier state infections the compositions may be administered in repeated dosages over a prolonged period of time, as necessary, to resolve or substantially mitigate the infection and/or shedding of virus.

Vaccine compositions for preventing HBV infection, particularly chronic HBV infection, are also provided. The vaccine compositions comprise an immunogenically effective amount of a HBV envelope peptide mentioned above which induces a MHC class I restricted cytotoxic T lymphocyte response, such as HLA-A2, and will typically further comprise an adjuvant, e.g., incomplete Freund's adjuvant or aluminum hydroxide. To achieve enhanced protection against HBV, the vaccine can further comprise components which elicit a protective antibody response to HBV envelope antigen.

In yet other embodiments the invention relates to methods for diagnosis, where the peptides of the invention are used to determine the presence of lymphocytes in an individual which are capable of a cytotoxic T cell response to HBV envelope antigen. The absence of such cells determines whether the individual of interest is susceptible to developing chronic HBV infection. Typically the lymphocytes are peripheral blood lymphocytes and the individual of interest is suffering from an acute HBV infection.

DESCRIPTION OF THE SPECIFIC EMBODIMENTS

Figure 1B:
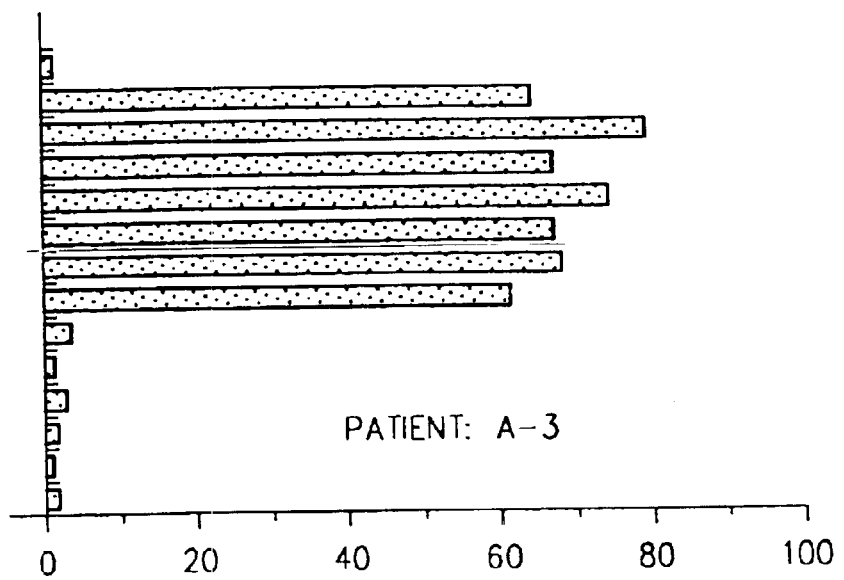
FIG. 1 shows that HBsAg335-343, WLSLLVPFV (SEQ ID NO:10), is the minimal optimal CTL epitope recognized by CTL stimulated HBsAg329-348. A CTL clone from patient A-1 and a CTL cloned line from patient A-3, generated by stimulation with HBsAg329-348, were tested against JY target ceiss prepulsed either with truncations (SEQ ID NOS:22 and 28–39, respectively) (upper panels) or with overlapping 9-mers or 10-mers (SEQ ID NOS:22, 40–50, 15, 10, 16, 51–55, 25, 56, 38 and 39, respectively) (lower lowers panels) covering HBsAg329-348.

The present invention provides peptides derived from HBV envelope proteins for use in compositions and methods for the treatment, prevention and diagnosis of HBV infection. The peptides stimulate MHC HLA-class I restricted cytotoxic T lymphocyte responses against HBV infected cells. The stimulated cytotoxic T lymphocytes are able to kill the infected cells or inhibit viral replication and thus interrupt or substantially prevent infection, including chronic HBV infection. A peptide effective in eliciting a cytotoxic T cell response may also be combined with an immunogen capable of eliciting a T-helper response.

The peptides employed in the invention are derived from the regions of HBenv183-191 (Seq. ID No. 1), HBenv248-260 (Seq. ID No. 2), HBenv260-269 (Seq. ID No. 9), HBenv335-343 (Seq. ID No. 10), HBenv152-161 (Seq. ID No. 11), HBenv177-185 (Seq. ID No. 12), HBenv204-212 (Seq. ID No. 13), and HBenv370-379 (Seq. ID No. 14), where the numbering is according to Galibert et al., supra.

By HBV cytotoxic T lymphocyte inducing "peptide" or "oligopeptide" of the present invention is meant a chain of at least four HBV amino acid sequence residues, preferably at least six, more preferably eight or nine, sometimes ten to twelve residues, and usually fewer than about fifty residues, more usually fewer than about thirty-five, and preferably fewer than twenty-five, e.g., eight to seventeen amino acid residues derived from an HBc sequence. It may be desirable to optimize peptides of the invention to a length of eight to twelve amino acid residues, commensurate in size with endogenously processed viral peptides that are bound to MHC class I molecules on the cell surface. See generally, Schumacher et al., *Nature* 350:703–706 (1991); Van Bleek et al., *Nature* 348:213–216 (1990); Rotzschke et al., *Nature* 348:252–254 (1990); and Falk et al., *Nature* 351:290–296 (1991), which are incorporated herein by reference. As set forth in more detail below, usually the peptides will have at least a majority of amino acids which are homologous to a corresponding portion of contiguous residues of the HBV sequences identified herein, and containing a CTL-inducing epitope.

The peptides can be prepared "synthetically," as described hereinbelow, or by recombinant DNA technology. Although the peptide will preferably be substantially free of other naturally occurring HBV proteins and fragments thereof, in some embodiments the peptides can be synthetically conjugated to native fragments or particles. The term peptide is used interchangeably with polypeptide in the present specification to designate a series of amino acids connected one to the other by peptide bonds between the alpha-amino and alpha-carboxy groups of adjacent amino acids. The polypeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

Desirably, the peptide will be as small as possible while still maintaining substantially all of the biological activity of the large peptide. By biological activity is meant the ability to bind an appropriate MHC molecule and induce a cytotoxic T lymphocyte response against HBV antigen or antigen mimetic. By a cytotoxic T lymphocyte response is meant a CD8+ T lymphocyte response specific for an HBV antigen of interest, wherein CD8+, MHC class I-restricted T lymphocytes are activated. The activated T lymphocytes secrete lymphokines (e.g., gamma interferon) liberate products (e.g., serine esterases) that inhibit viral replication in infected autologous cells or transfected cells, with or without cell killing.

The terms "homologous", "substantially homologous", and "substantial homology" as used herein denote a sequence of amino acids having at least 50% identity wherein one sequence is compared to a reference sequence of amino acids. The percentage of sequence identity or homology is calculated by comparing one to another when aligned to corresponding portions of the reference sequence.

A CTL-inducing HBV peptide embodiment of the invention from the nucleocapsid region comprises from six to thirty-five amino acids and contains at least one HLA-restricted CTL epitopic site from the peptide region HBenv183-191 (Seq. ID No. 1). A majority of the amino acids of the peptide will be identical or substantially homologous to the amino acids of the corresponding portions of the naturally occurring HBenv183-191 region, where HBenv183-191 has the sequence:

HBenv183-191 (Seq. ID No. 1) Phe-Leu-Leu-Thr-Arg-Ile-Leu-Thr-Ile

The peptide embodiments of this HBenv183-191 region can be optionally flanked and/or modified at one or both of the N- and C-termini, as desired, by amino acids from HBV sequences, including HBc, amino acids added to facilitate linking, other N- and C-terminal modifications, linked to carriers, etc., as further described herein. The peptide HBenv183-191 induces a cytotoxic T lymphocyte response which is mediated by at least the MHC class I molecule HLA-A2.

Other HBenv peptide embodiments of the invention are prepared from the region of HBenv248-260. Peptides derived from this region contain at least one CTL-inducing HLA class I-restricted epitopic site, and will typically be at least seven amino acids, more usually nine, ten or eleven amino acids or more. A majority of the amino acids of the peptide will be identical or substantially homologous to the amino acids of the corresponding portions of the naturally occurring HBenv248-260 sequence, where HBenv248-260 has the sequence (for HBV subtype ayw):

HBenv248-260 (Seq. ID No. 2) Phe-Ile-Leu-Leu-Leu-Cys-Leu-Ile-Phe-Leu-Leu-Val-Leu.

The peptide from the HBenv248-260 region can be flanked and/or modified at one or both termini as described herein.

Representative CTL-inducing peptides prepared from the region of HBenv248-260 include the following 9- and 10-mer peptides:

HBenv248-257 (Seq. ID No. 3) Phe-Ile-Leu-Leu-Leu-Cys-Leu-Ile-Phe-Leu;

HBenv249-257 (Seq. ID No. 4) Ile-Leu-Leu-Leu-Cys-Leu-Ile-Phe-Leu;

HBenv249-258 (Seq. ID No. 5) Ile-Leu-Leu-Leu-Cys-Leu-Ile-Phe-Leu-Leu;

HBenv250-258 (Seq. ID No. 6) Leu-Leu-Leu-Cys-Leu-Ile-Phe-Leu-Leu;

HBenv251-259 (Seq. ID No. 7) Leu-Leu-Cys-Leu-Ile-Phe-Leu-Leu-Val;

HBenv251-260 (Seq. ID No. 8) Leu-Leu-Cys-Leu-Ile-Phe-Leu-Leu-Val-Leu;

The foregoing peptides contain a HLA-restricted CTL-inducing epitope, typically at least HLA-A2 restricted, and can be flanked and/or modified at one or both termini as mentioned for peptide I above.

In a further embodiment, a peptide of the invention comprises the 10-mer peptide HBenv260-269, and peptides derived from HBenv260-269 which contain a CTL-inducing HLA class I-restricted epitopic site(s) of at least seven contiguous amino acids. A majority of the amino acids of the peptide will be identical or substantially homologous to the amino acids of the corresponding portions of the naturally occurring HBenv260-269 sequence, where HBenv260-269 has the sequence:

HBenv260-269 (Seq. ID No. 9) Leu-Leu-Asp-Tyr-Gln-Gly-Met-Leu-Pro-Val.

A peptide prepared from this region can be flanked and/or modified at one or both termini as described herein. The peptide HBenv260-269 (Seq. ID No. 4) induces a cytotoxic T lymphocyte response which is mediated by at least the MHC class I HLA-A2 molecule.

Yet other CTL-inducing peptides of the invention are from the region of HBenv335-343 (Seq. ID No. 10), and includes peptides derived from HBenv335-343 (Seq. ID No. 10) which contain one or more CTL-inducing HLA class I-restricted epitopic site(s) of at least seven contiguous amino acids. A majority of the amino acids of the peptide will be identical or substantially homologous to the amino acids of the corresponding portions of the naturally occurring HBenv335-343 sequence, where HBenv335-343 has the sequence:

HBenv335-343 (Seq. ID No. 10) Trp-Leu-Ser-Leu-Leu-Val-Pro-Phe-Val, wherein the selected peptide can be flanked and/or modified at one or both termini as described herein.

Yet other CTL-inducing peptides of the invention are from the region of HBenv152-161 (Seq. ID No. 11), and includes peptides derived from HBenv152-161 (Seq. ID No. 11) which contain one or more CTL-inducing HLA class I-restricted epitopic site(s) of at least seven contiguous amino acids. A majority of the amino acids of the peptide will be identical or substantially homologous to the amino acids of the corresponding portions of the naturally occurring HBenv152-161 sequence, where HBenv152-161 has the sequence (adw subtype]):

HBenv152-161 (Seq. ID No. 11) Ser-Ile-Leu-Ser-Lys-Thr-Gly-Asp-Pro-Val, wherein the selected peptide can be flanked and/or modified at one or both termini as described herein.

Other CTL-inducing peptides of the invention are from the region of HBenv177-185 (Seq. ID No. 12), and includes peptides derived from HBenv177-185 (Seq. ID No. 12) which contain one or more CTL-inducing HLA class I-restricted epitopic site(s) of at least seven contiguous amino acids. A majority of the amino acids of the peptide will be identical or substantially homologous to the amino acids of the corresponding portions of the naturally occurring HBenv177-185 sequence, where HBenv177-185 has the sequence (adw subtype):

HBenv177-185 (Seq. ID No. 12) Val-Leu-Gln-Ala-Gly-Phe-Phe-Leu-Leu, wherein the selected peptide can be flanked and/or modified at one or both termini as described herein.

Additional CTL-inducing peptides of the invention are from the region of HBenv204-212 (Seq. ID No. 13), and includes peptides derived from HBenv204-212 (Seq. ID No. 13) which contain one or more CTL-inducing HLA class I-restricted epitopic site(s) of at least seven contiguous amino acids. A majority of the amino acids of the peptide will be identical or substantially homologous to the amino acids of the corresponding portions of the naturally occurring HBenv204-212 sequence, where HBenv204-212 has the sequence (adw subtype):

HBenv204-212 (Seq. ID No. 13) Phe-Leu-Gly-Gly-Thr-Pro-Val-Cys-Leu, wherein the selected peptide can be flanked and/or modified at one or both termini as described herein.

Additional CTL-inducing peptides of the invention are from the region of HBenv370-379 (Seq. ID No. 14), and includes peptides derived from HBenv370-379 (Seq. ID No. 14) which contain one or more CTL-inducing HLA class I-restricted epitopic site(s) of at least seven contiguous amino acids. A majority of the amino acids of the peptide will be identical or substantially homologous to the amino acids of the corresponding portions of the naturally occurring HBenv370-379 sequence, where HBenv370-379 has the sequence (adw subtype):

HBenv370-379 (Seq. ID No. 14) Ser-Ile-Val-Ser-Pro-Phe-Ile-Pro-Leu-Leu, wherein the selected peptide can be flanked and/or modified at one or both termini as described herein.

As mentioned above, additional amino acids can be added to the termini of an oligopeptide or peptide to provide for ease of linking peptides one to another, for coupling to a carrier, support or a larger peptide, for reasons discussed herein, or for modifying the physical or chemical properties of the peptide or oligopeptide, and the like. Amino acids such as tyrosine, cysteine, lysine, glutamic or aspartic acid, and the like, can be introduced at the C- or N-terminus of the peptide or oligopeptide. In addition, the peptide or oligopeptide sequences can differ from the natural sequence by being modified by terminal-$NH_2$ acylation, e.g., acetylation, or thioglycolic acid amidation, terminal-carboxy amidation, e.g., ammonia, methylamine, etc. In some instances these modifications may provide sites for linking to a support or other molecule.

It will be understood that the HBV peptides of the present invention or analogs thereof which have cytotoxic T lymphocyte stimulating activity may be modified as necessary to provide certain other desired attributes, e.g., improved pharmacological characteristics, while increasing or at least retaining substantially the biological activity of the unmodified peptide. For instance, the peptides can be modified by extending, decreasing or substituting amino acids in the peptide sequence by, e.g., the addition or deletion of amino acids on either the amino terminal or carboxy terminal end, or both, of peptides derived from the sequences disclosed herein. The peptides may be modified to substantially enhance the CTL inducing activity, such that the modified peptide analogs have CTL activity greater than a peptide of the wild-type sequence. For example, it may be desirable to increase the hydrophobicity of the N-terminal of a peptide, particularly where the second residue of the N-terminal is hydrophobic and is implicated in binding to the HLA restriction molecule. By increasing hydrophobicity at the N-terminal, the efficiency of the presentation to T cells may be increased. Peptides prepared from other disease associated antigens, particularly those containing CTL inducing epitopes for which a host may not have significant CTL activity, may be made CTL-inducing by substituting hydrophobic residues at the N-terminus of the peptide where the second residue is normally hydrophobic.

The peptides employed in the subject invention need not be identical to peptides HBenv183-191 (Seq. ID No. 1), HBenv248-257 (Seq. ID No. 3), HBenv249-257 (Seq. ID No. 4), HBenv249-258 (Seq. ID No. 5), HBenv250-258 (Seq. ID No. 6) HBenv251-259 (Seq. ID No. 7), HBenv251-260 (Seq. ID No. 8), HBenv260-269 (Seq. ID No. 9), HBenv335-343 (Seq. ID No. 10), HBenv152-161 (Seq. ID No. 11), HBenv177-185 (Seq. ID No. 12), HBenv204-212 (Seq. ID No. 13), or HBenv370-379 (Seq. ID No. 14), so long as the subject compounds are able to provide for cytotoxic T lymphocytic activity against at least one of the four major subtypes of HBV. Although different strains of HBV exist, they each share at least one common envelope determinant, which is designated "a". Each strain also has two other envelope determinants, one of which is either "d" or "y", and the second is either "w" or "r". Thus, there are four possible subtypes of the virus: adw, ayw, adr, and ayr. The cloning, sequencing and expression of HBV are described in GB 2034323, EP 13828, U.S. Pat. No. 4,935,235, and the complete sequence of the HBV envelope region is also described in Galibert et al., *Nature* 281:646 (1979), each of the foregoing being incorporated herein by reference. Amino acid sequences are described in the GenBank-72 database for 20 different HBV strains, including 7 of the adw subtype, 5 of the ayw subtype, 7 of the adr subtype, and 1 strain of the ayr subtype, the GenBank sequences also being incorporated herein by reference.

Therefore, the peptides may be subject to various changes, such as insertions, deletions, and substitutions, either conservative or non-conservative, where such changes provide for certain advantages in their use. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Usually, the portion of the sequence which is intended to substantially mimic an HBV cytotoxic T lymphocyte stimulating epitope will not differ by more than about 20% from the sequence of at least one subtype of HBV, except where additional amino acids may be added at either terminus for the purpose of modifying the physical or chemical properties of the peptide for, e.g., ease of linking or coupling, and the like. Where regions of the peptide sequences are found to be polymorphic among HBV subtypes, it may be desirable to vary one or more particular amino acids to more effectively mimic differing cytotoxic T-lymphocyte epitopes of different HBV strains or subtypes.

Within the peptide sequences identified by the present invention, including the representative peptides listed above, there are residues (or those which are substantially functionally equivalent) which allow the peptide to retain their biological activity, i.e., the ability to stimulate a class I-restricted cytotoxic T-lymphocytic response against HBV infected cells or cells which express HBV antigen. These residues can be identified by single amino acid substitutions, deletions, or insertions. In addition, the contributions made by the side chains of the residues can be probed via a systematic scan with a specified amino acid (e.g., Ala). Peptides which tolerate multiple substitutions generally incorporate such substitutions as small, relatively neutral molecules, e.g., Ala, Gly, Pro, or similar residues. The number and types of residues which can be substituted, added or subtracted will depend on the spacing necessary between the essential epitopic points and certain conformational and functional attributes which are sought (e.g., hydrophobicity vs. hydrophilicity). If desired, increased binding affinity of peptide analogues to its MHC molecule for presentation to a cytotoxic T-lymphocyte can also be achieved by such alterations. Generally, any spacer substitutions, additions or deletions between epitopic and/or conformationally important residues will employ amino acids or moieties chosen to avoid steric and charge interference which might disrupt binding.

Peptides which tolerate multiple substitutions while retaining the desired biological activity may also be synthesized as D-amino acid containing peptides. Such peptide may be synthesized as "inverso" or "retro-inverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptide. Further, L-amino acid-containing peptides with or without substitutions can be capped with a D-amino acid to inhibit exopeptidase destruction of the antigenic peptide.

In addition to the exemplary peptides described herein, the invention provides methods for identifying other epitopic regions associated with said peptide regions capable of inducing MHC-restricted cytotoxic T lymphocyte responses against HBV. The methods comprise obtaining peripheral blood lymphocytes (PBL) from infected or uninfected individuals and exposing (stimulating) the cells with synthetic peptide or polypeptide fragments derived from a peptide region of HBenv183-191 (Seq. ID No. 1), HBenv248-260 (Seq. ID No. 2), HBenv260-269 (Seq. ID No. 9), HBenv335-343 (Seq. ID No. 10), HBenv152-161 (Seq. ID No. 11), HBenv177-185 (Seq. ID No. 12), HBenv204-212 (Seq. ID No. 13), or HBenv370-379 (Seq. ID No. 14). Pools of overlapping synthetic peptides, each typically about 8 to 20 residues long, preferably 9–12 residues, can be used to stimulate the cells. Active peptides can be selected from pools which induce cytotoxic T lymphocyte activity. The ability of the peptides to induce specific cytotoxic activity is determined by incubating the stimulated PBL with autologous labeled (e.g., $^{51}Cr$) target cells (such as HLA matched macrophages, T cells, fibroblasts or B lymphoblastoid cells) infected or transfected with the HBV subgenomic fragments thereof, such that the targeted antigen is synthesized endogenously by the cell (or the cell is pulsed with the peptide of interest), and measuring specific release of label.

Once a peptide having an epitopic region which stimulates a cytotoxic T lymphocyte response is identified, the MHC restriction element of the response can be determined. This involves incubating the stimulated PBL or short term lines thereof with a panel of (labeled) target cells of known HLA types which have been pulsed with the peptide of interest, or appropriate controls. The HLA allele(s) of cells in the panel which are lysed by the CTL are compared to cells not lysed, and the HLA restriction element(s) for the cytotoxic T lymphocyte response to the antigen of interest is identified.

Carbone et al., *J. Exp. Med.* 167:1767 (1988), have reported that stimulation with peptides may induce cytotoxic T lymphocytes with low affinity for corresponding endogenous protein, such that repetitive peptide stimulation may yield cytotoxic T lymphocytes that recognize peptide but not native antigen. As the inability of stimulated cytotoxic T lymphocytes to recognize native HBV proteins would be undesirable in the development of HBV peptide therapeutics and vaccine compositions, methods to circumvent this potential limitation are used. A sequential restimulation of cytotoxic T cells is employed in the present invention to identify and select T cells with a higher affinity for naturally processed antigen than for a synthetic peptide. Short term cytotoxic T lymphocyte lines are established by restimulating activated PBL. Cells stimulated with peptide are restimulated with peptide and recombinant or native HBV antigen, e.g., HBsAg. Cells having activity are also stimulated with an appropriate T cell mitogen, e.g., phytohemagglutinin (PHA). The restimulated cells are provided with irradiated allogeneic PBLs as an antigen nonspecific source of T cell help, and HBV antigen. To selectively expand the population of cytotoxic T lymphocytes that recognize native HBV antigen and to establish long term lines, PBL from a patient are first stimulated with peptide and recombinant or native HBV antigen, followed by restimulation with HLA-matched B lymphoblastoid cells that stably express the corresponding HBV antigen polypeptide. The cell lines are re-confirmed for the ability to recognize endogenously synthesized antigen using autologous and allogeneic B-lymphoblastoid or other cells transfected or infected with appropriate antigen.

Having identified different peptides of the invention which contribute to inducing anti-HBV cytotoxic T lymphocyte responses in one or more patients or HLA types, in some instances it may be desirable to join two or more peptides in a composition. The peptides in the composition can be identical or different, and together they should provide equivalent or greater biological activity than the parent peptide(s). For example, using the methods described herein, two or more peptides may define different or overlapping cytotoxic T lymphocyte epitopes from a particular region, e.g., the HBenv248-257 (Seq. ID No. 3), HBenv249-257 (Seq. ID No. 4), HBenv249-258 (Seq. ID No. 5), HBenv250-258 (Seq. ID No. 6) HBenv251-259 (Seq. ID No. 7), and/or HBenv251-260 (Seq. ID No. 8) peptides, which peptides can be combined in a "cocktail" to provide enhanced immunogenicity for cytotoxic T lymphocyte responses. Moreover, peptides of one region can be combined with peptides of other HBV regions, from the same or different HBV protein, particularly when a second or subsequent peptide has a MHC restriction element different from the first. Other CTL-inducing HBV peptides are described in co-pending application U.S. Ser. No. 07/935, 898, which is incorporated herein by reference. This composition of peptides can be used to effectively broaden the immunological coverage provided by therapeutic, vaccine or diagnostic methods and compositions of the invention among a diverse population. For example, the different frequencies of HLA alleles among prevalent ethnic groups (caucasian, asian and african blacks) are shown in Table I below. Therapeutic or vaccine compositions of the invention may be formulated to provide potential therapy or immunity to as high a percentage of a population as possible.

TABLE I

HLA ALLELE FREQUENCIES AMONG PREVALENT ETHNIC GROUPS

| HLA Allele | EUC | NAC | AFR | JPN |
|---|---|---|---|---|
| A2 | 45.3 | 46.6 | 27.3 | 43.2 |
| A29 | 7.4 | 8.1 | 12.3 | 0.4 |
| A31 | 5.4 | 6.2 | 4.4 | 15.3 |
| A32 | 8.8 | 7.1 | 3 | 0.1 |
| A33 | 3.3 | 3.4 | 9 | 13.1 |
| A28* | 7.7 | 9.9 | 16.6 | 1.1 |

Abbreviations: EUC, European Caucasian; NAC, North American Caucasian; AFR, African blacks; JPN, Japanese.
*A28 represents the two alleles Aw68 and Aw69

The peptides of the invention can be combined via linkage to form polymers (multimers), or can be formulated in a composition without linkage, as an admixture. Where the same peptide is linked to itself, thereby forming a homopolymer, a plurality of repeating epitopic units are presented. When the peptides differ, e.g., a cocktail representing different HBV subtypes, different epitopes within a subtype, different HLA restriction specificities, a peptide which contains T helper epitopes, heteropolymers with repeating units are provided. In addition to covalent linkages, noncovalent linkages capable of forming intermolecular and intrastructural bonds are included.

Linkages for homo- or hetero-polymers or for coupling to carriers can be provided in a variety of ways. For example, cysteine residues can be added at both the amino- and carboxy-termini, where the peptides are covalently bonded via controlled oxidation of the cysteine residues. Also useful are a large number of heterobifunctional agents which generate a disulfide link at one functional group end and a peptide link at the other, including N-succidimidyl-3-(2-pyridyldithio) proprionate (SPDP). This reagent creates a disulfide linkage between itself and a cysteine residue in one protein and an amide linkage through the amino on a lysine or other free amino group in the other. A variety of such disulfide/amide forming agents are known. See, for example, Immun. Rev. 62:185 (1982), which is incorporated herein by reference. Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl) cyclohexane-1-carboxylic acid and the like. The carboxyl groups can be activated by combining them with succinimide or 1-hydroxy-2-nitro-4-sulfonic acid, sodium salt. A particularly preferred coupling agent is succinimidyl 4-(N-maleimidomethyl) cyclohexane-1-carboxylate (SMCC). It will be understood that linkage should not substantially interfere with either of the linked groups to function as described, e.g., as an HBV cytotoxic T cell determinant, peptide analogs, or T helper determinant.

In another aspect the peptides of the invention can be combined or coupled with other peptides which present HBV T-helper cell epitopes, i.e., epitopes which stimulate T cells that cooperate in the induction of cytotoxic T cells to HBV. The T-helper cells can be either the T-helper 1 or T-helper 2 phenotype, for example. T-helper epitopes from HBV sequences have been identified at HBc1-20, having the sequence: Met-Asp-Ile-Asp-Pro-Tyr-Lys-Glu-Phe-Gly-Ala-Thr-Val-Glu-Leu-Leu-Ser-Phe-Leu-Pro (Seq. ID No. 17). Other T-helper epitopes are provided by peptides from the region HBc50-69, having the sequence Pro-His-His-Tyr-Ala-Leu-Arg-Gln-Ala-Ile-Leu-Cys-Trp-Gly-Glu-Leu-Met-Tyr-Leu-Ala (Seq. ID No. 18), and from the region of HBc100-139, including HBc100-119 having the sequence Leu-Leu-Trp-Phe-His-Ile-Ser-Cys-Leu-Thr-Phe-Gly-Arg-Glu-Thr-Val-Ile-Glu-Tyr-Leu (Seq. ID No. 19) (where $Ile_{116}$ is Leu in the HBV adw subtype), HBc117-131 having the sequence Glu-Tyr-Leu-Val-Ser-Phe-Gly-Val-Trp-Ile-Arg-Thr-Pro-Pro-Ala (Seq. ID No. 20), and peptide HBc120-139 having the sequence Val-Ser-Phe-Gly-Val-Trp-Ile-Arg-Thr-Pro-Pro-Ala-Tyr-Arg-Pro-Pro-Asn-Ala-Pro-Ile (Seq. ID No. 21). See, Ferrari et al., J. Clin. Invest. 88:214–222 (1991), and U.S. Pat. No. 4,882,145, each incorporated herein by reference.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co. (1984); Tam et al., J. Am. Chem. Soc. 105:6442 (1983); Merrifield, Science 232:341–347 (1986); and Barany and Merrifield, The Peptides, Gross and Meienhofer, eds., Academic Press, New York, pp. 1–284 (1979), each of which is incorporated herein by reference.

Alternatively, recombinant DNA technology may be employed wherein a nucleotide sequence which encodes a peptide of interest is inserted into an expression vector, transformed or transfected into an appropriate host cell and cultivated under conditions suitable for expression. These procedures are generally known in the art, as described generally in Sambrook et al., Molecular Cloning. A Laboratory Manual, Cold Spring Harbor Press, Cold Spring Harbor, N.Y. (1982), and Ausubel et al., (ed.) Current Protocols in Molecular Biology, John Wiley and Sons, Inc., New York (1987), and U.S. Pat. Nos. 4,237,224, 4,273,875, 4,431,739, 4,363,877 and 4,428,941, for example, whose disclosures are each incorporated herein by reference. Thus, fusion proteins which comprise one or more peptide sequences of the invention can be used to present the HBV cytotoxic T cell determinants. For example, a recombinant envelope protein of the invention is prepared in which the HBenv amino acid sequence is altered so as to more effectively present epitopes of peptide regions described herein to stimulate a cytotoxic T lymphocyte response. By this means a polypeptide is used which incorporates several T cell epitopes.

As the coding sequence for peptides of the length contemplated herein can be synthesized by chemical techniques, for example, the phosphotriester method of Matteucci et al., J. Am. Chem. Soc. 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Yeast or mammalian cell hosts may also be used, employing suitable vectors and control sequences.

The peptides of the present invention and pharmaceutical and vaccine compositions thereof are useful for administration to mammals, particularly humans, to treat and/or prevent HBV infection. As the peptides are used to stimulate cytotoxic T-lymphocyte responses to HBV infected cells, the compositions can be used to treat or prevent acute and/or chronic HBV infection.

For pharmaceutical compositions, the peptides of the invention as described above will be administered to an individual already infected with HBV. Those in the incubation phase or the acute phase of infection can be treated with the immunogenic peptides separately or in conjunction with other treatments, as appropriate. In therapeutic applications, compositions are administered to a patient in an amount sufficient to elicit an effective cytotoxic T lymphocyte response to HBV and to cure or at least partially arrest its symptoms and/or complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician, but generally range from about 1 µg to about 2,000 mg of peptide for a 70 kg patient, with dosages of from about 10 µg to about 100 mg of peptide being more commonly used, followed by booster dosages from about 1 µg to about 1 mg of peptide over weeks to months, depending on a patient's CTL response, as determined by measuring HBV-specific CTL activity in PBLs obtained from the patient. It must be kept in mind that the peptides and compositions of the present invention may generally be employed in serious disease states, that is, life-threatening or potentially life threatening situations. In such cases, in view of the minimization of extraneous substances and the relative nontoxic nature of the peptides, it is possible and may be felt desirable by the treating physician to administer substantial excesses of these peptide compositions.

Single or multiple administrations of the compositions can be carried out with dose levels and pattern being selected by the treating physician. In any event, the pharmaceutical formulations should provide a quantity of cytotoxic T-lymphocyte stimulatory peptides of the invention sufficient to effectively treat the patient.

For therapeutic use, administration should begin at the first sign of HBV infection or shortly after diagnosis in cases of acute infection, and continue until at least symptoms are substantially abated and for a period thereafter. In well established and chronic cases, loading doses followed by maintenance or booster doses may be required. The elicitation of an effective cytotoxic T lymphocyte response to HBV during treatment of acute hepatitis will minimize the possibility of subsequent development of chronic hepatitis, HBV carrier stage, and ensuing hepatocellular carcinoma.

Treatment of an infected individual with the compositions of the invention may hasten resolution of the infection in acutely infected individuals, about 90% of whom are capable of resolving the infection naturally. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The peptide compositions can also be used for the treatment of chronic hepatitis and to stimulate the immune system of carriers to substantially reduce or even eliminate virus-infected cells. Those with chronic hepatitis can be identified as testing positive for virus from about 3–6 months after infection. As individuals may develop chronic HBV infection because of an inadequate (or absent) cytotoxic T lymphocyte response during the acute phase of their infection, it is important to provide an amount of immunopotentiating peptide in a formulation and mode of administration sufficient to effectively stimulate a cytotoxic T cell response. Thus, for treatment of chronic hepatitis, a representative dose is in the range of about 1 µg to 1,000 mg, preferably about 5 µg to 100 mg for a 70 kg patient per dose. Administration should continue until at least clinical symptoms or laboratory indicators indicate that the HBV infection has been eliminated or substantially abated and for a period thereafter. Immunizing doses followed by maintenance or booster doses at established intervals, e.g., from one to four weeks, may be required, possibly for a prolonged period of time, as necessary to resolve the infection. For the treatment of chronic and carrier HBV infection it may also be desirable to combine the CTL peptides with other peptides or proteins that induce immune response to other HBV antigens.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the cytotoxic T-lymphocyte stimulatory peptides dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

In some embodiments it may be desirable to include in the pharmaceutical composition at least one component which primes CTL. Lipids have been identified which are capable of priming CTL in vivo against viral antigens, e.g., tripalmitoyl-S-glycerylcysteinly-seryl-serine ($P_3CSS$), which can effectively prime virus specific cytotoxic T lymphocytes when covalently attached to an appropriate peptide. See, Deres et al., *Nature* 342:561–564 (1989), incorporated herein by reference. Peptides of the invention can be coupled to $P_3CSS$, for example, and the lipopeptide administered to an individual to specifically prime a cytotoxic T lymphocyte response to HBV. Further, as the induction of neutralizing antibodies can also be primed with $P_3CSS$ conjugated to a peptide which displays an appropriate epitope, e.g., HBsAg epitopes, the two compositions can be combined to more effectively elicit both humoral and cell-mediated responses to HBV infection.

The concentration of cytotoxic T-lymphocyte stimulatory peptides of the invention in the pharmaceutical formulations can vary widely, i.e., from less than about 1%, usually at or at least about 10% to as much as 20 to 50% or more by weight, and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 100 mg of peptide. Actual methods for preparing parenterally administrable compounds will be known or apparent to those skilled in the art and are described in more detail in for example, *Remington's Pharmaceutical Science*, 17th ed., Mack Publishing Company, Easton, Pa. (1985), which is incorporated herein by reference.

The peptides of the invention may also be administered via liposomes, which serve to target the peptides to a particular tissue, such as lymphoid tissue or HBV-infected hepatic cells. Liposomes can also be used to increase the half-life of the peptide composition. Liposomes useful in the present invention include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor, prevalent among lymphoid cells, such as monoclonal antibodies which bind to the CD45 antigen, or with other therapeutic or immunogenic compositions. Thus, liposomes filled with a desired peptide of the invention can be directed to the site of lymphoid or hepatic cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size and stability of the liposomes in the blood stream. A variety of methods are available for preparing liposomes, as described in, e.g., Szoka et al., *Ann. Rev. Biophys. Bioeng.* 9:467 (1980), U.S. Pat. Nos. 4,235,871, 4,501,728, 4,837,028, and 5,019,369, incorporated herein by reference. For targeting to the immune cells, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, the mode of administration, the peptide being delivered, the stage of disease being treated, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, the cytotoxic T-lymphocyte stimulatory peptides are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included as desired, e.g., lecithin for intranasal delivery.

In another aspect the present invention is directed to vaccines which contain as an active ingredient an immunogenically effective amount of a cytotoxic T-lymphocyte stimulating peptide as described herein. The peptide(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or cytotoxic T cells that react with different antigenic determinants of HBV. Useful carriers are well known in the art, and include, e.g., keyhole limpet hemocyanin, thyroglobulin, albumins such as human serum albumin, tetanus toxoid, polyamino acids such as poly(D-lysine:D-glutamic acid), and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. And, as mentioned above, cytotoxic T lymphocyte responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of cytotoxic T-lymphocytes specific for HBV antigen, and the host becomes at least partially immune to HBV infection, or resistant to developing chronic HBV infection.

Vaccine compositions containing the peptides of the invention are administered to a patient susceptible to or otherwise at risk of HBV infection to enhance the patient's own immune response capabilities. Such an amount is defined to be a "immunogenically effective dose." In this use, the precise amounts again depend on the patient's state of health and weight, the mode of administration, the nature of the formulation, etc., but generally range from about 1.0 $\mu$g to about 500 mg per 70 kilogram patient, more commonly from about 50 $\mu$g to about 200 mg per 70 kg of body weight. The peptides are administered to individuals of an appropriate HLA type, e.g., for vaccine compositions of peptides from the region of HBenv183-191 (Seq. ID No. 1), HBenv248-260 (Seq. ID No. 2), HBenv260-269 (Seq. ID No. 9), HBenv335-343 (Seq. ID No. 10), HBenv152-161 (Seq. ID No. 11), HBenv177-185 (Seq. ID No. 12), HBenv204-212 (Seq. ID No. 13), and/or HBenv370-379 (Seq. ID No. 14), these will be administered to at least HLA-A2 individuals.

In some instances it may be desirable to combine the peptide vaccines of the invention with vaccines which induce neutralizing antibody responses to HBV, particularly to HBV envelope antigens, such as recombinant HBV env-encoded antigens or vaccines prepared from purified plasma preparations obtained from HBV-infected individuals. A variety of HBV vaccine preparations have been described, and are based primarily on HBsAg and polypeptide fragments thereof. For examples of vaccines which can be formulated with the peptides of the present invention, see generally, EP 154,902 and EP 291,586, and U.S. Pat. Nos. 4,565,697, 4,624,918, 4,599,230, 4,599,231, 4,803,164, 4,882,145, 4,977,092, 5,017,558 and 5,019,386, each being incorporated herein by reference. The vaccines can be combined and administered concurrently, or as separate preparations.

For therapeutic or immunization purposes, the peptides of the invention can also be expressed by attenuated viral hosts, such as vaccinia. This approach involves the use of vaccinia virus as a vector to express nucleotide sequences that encode the HBV peptides of the invention. Upon introduction into an acutely or chronically HBV-infected host or into a non-infected host, the recombinant vaccinia virus expresses the HBV peptide and thereby elicits a host cytotoxic T lymphocyte response to HBV. Vaccinia vectors and methods useful in immunization protocols are described in, e.g., U.S. Pat. No. 4,722,848, incorporated herein by reference. Another vector is BCG (bacille Calmette Guerin). BCG vectors are described in Stover et al. (*Nature* 351:456–460 (1991)) which is incorporated herein by reference. A wide variety of other vectors useful for therapeutic administration or immunization of the peptides of the invention, e.g., *Salmonella typhi* vectors and the like, will be apparent to those skilled in the art from the description herein.

The compositions and methods of the claimed invention may be employed for ex vivo therapy. By ex vivo therapy is meant that therapeutic or immunogenic manipulations are performed outside the body. For example, lymphocytes or other target cells may be removed from a patient and treated with high doses of the subject peptides, providing a stimulatory concentration of peptide in the cell medium far in excess of levels which could be accomplished or tolerated by the patient. Following treatment to stimulate the CTLs, the cells are returned to the host to treat the HBV infection. The host's cells may also be exposed to vectors which carry genes encoding the peptides, as described above. Once transfected with the vectors, the cells may be propagated in vitro or returned to the patient. The cells which are propagated in vitro may be returned to the patient after reaching a predetermined cell density.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic HBV infection.

The following examples are offered by way of illustration, not by way of limitation.

EXAMPLE I

Identification of CTL-specific HBenv Epitopes

This Example describes the identification of HBenv peptides which stimulated HLA-restricted CTL responses specific for HBV envelope antigens.

All patients included in the study were HLA-A2 positive. Thirteen patients (A-1 to A-13; Table II) were studied during an episode of acute hepatitis, 6 (C-1 to C-6) were chronically infected by HBV, and 6 uninfected healthy volunteers (N-1 to N-6) served as normal controls. The patients and their HLA haplotypes, determined using PBMC in microcytotoxicity testing with HLA typing trays (One Lambda, Canoga Park, Calif.), are shown in Table II.

Diagnosis of acute hepatitis was based on standard diagnostic criteria. Diagnostic parameters included clinical (jaundice) and biochemical evidence of liver injury (ALT activity at least 20 fold greater than the upper limits of normal), together with serological evidence of acute HBV infection (presence of HBV surface antigen (HBsAg) and IgG anti-HBc antibody) in the absence of serological evidence of hepatitis delta and hepatitis C virus infection (Abbott Laboratories, North Chicago, Ill.). All patients were studied during the first 4 weeks after onset of jaundice, at which time their serum was positive for HBsAg and their ALT levels were markedly abnormal. Eleven of the 13 patients subsequently recovered from the illness, with normalization of serum transaminase and clearance of HBsAg within four months of initial diagnosis. One patient (A-11, Table II) developed chronic active hepatitis and remained HBsAg positive 13 months after initial diagnosis. One patient (A-10) was lost to follow-up after the initial clinic visit. Patients with chronic hepatitis B were repeatedly serologically positive for HBsAg for more than six months and displayed mildly to moderately elevated serum ALT activity. Normal controls had no clinical history of HBV infection and were serologically negative for HBV markers. All patients and

TABLE II

Characteristics of Subjects Studied

| Subject | Sex | Diagnosis | HLA class I haplotype |
|---|---|---|---|
| A-1 | Male | Acute | A2, A30, B35, B44, Cw4, Cw7 |
| A-2 | Male | Acute | A2, A31, 8w58(5Y), B51, Cw3 |
| A-3 | Male | Acute | A2, Bw41, Bw71, Cw4, Cw7 |
| A-4 | Male | Acute | A2, A32, Bw41, Bw71, Cw4, Cw7 |
| A-5 | Male | Acute | A2, A1, B8, 8w58(5Y), Cw7 |
| A-6 | Female | Acute | A2, Aw68, B35, Cw3, Cw4 |
| A-7 | Male | Acute | A2, A1, B8, Bw73, Cw3, Cw4 |
| A-8 | Female | Acute | A2, Aw69, Bw53, Cw4 |
| A-9 | Male | Acute | A2, A24, B7, B27, Cw2, Cw7 |
| A-10 | Male | Acute | A2, A3, Bw62, Bw71, Cw3, Cw4 |
| A-11 | Male | Acute | A2, A24, B35, Cw4 |
| A-12 | Male | Acute | A2, A3, Cw5 |
| A-13 | Male | Acute | A2, A3, B7, Bw60, Cw3, Cw7 |
| C-1 | Male | Chronic | A2, B27, B35, Cw2, Cw4 |
| C-2 | Male | Chronic | A2, A1, B8, B44 |
| C-3 | Male | Chronic | A2, A24, B44, Bw67 |
| C-4 | Male | Chronic | A2, Aw69, Bw41, Bw52 |
| C-5 | Male | Chronic | A2, B5, Bw62, Cw4 |
| C-6 | Male | Chronic | A2, A26, B35, Cw4 |
| N-1 | Male | Normal | A2, A11, B44, Cw4 |
| N-2 | Male | Normal | A2, Bw56, B35 |
| N-3 | Male | Normal | A2, A11, B8, Bw62, Cw4 |
| N-4 | Male | Normal | A2, A23, B5, Bw58, Cw2, Cw6 |
| N-5 | Male | Normal | A2, B44, Bw63 |
| N-6 | Female | Normal | A2, A11, Bw58 | normal controls were serologically negative for antibody to HIV.

PBMC from patients and normal donors were separated on Ficoll-Hypaque density gradients (Sigma, St. Louis, Mo.), washed three times in Hanks balanced salt solution (HBSS) (Gibco, Grand Island, N.Y.), resuspended in RPMI 1640 medium (Gibco, Grand Island, N.Y.) supplemented with L-glutamine (2 mM), gentamicin (10 μg/ml), penicillin (50 U/ml), streptomycin (50 μg/ml), and HEPES (5 mM) containing 10% heat inactivated human AB serum (complete medium) and plated in 24 well plates at 4×10$^6$ cells/well. The synthetic peptides were added to the cell cultures at a final concentration of 10 μg/ml unless otherwise noted. rHBcAg was added at 1 μg/ml during the first week of stimulation. At day 3, 1 ml of complete medium supplemented with rIL2 (Hoffman-La Roche, Nutley, N.Y.) at 10 U/ml final concentration was added in each well. On day 7, the cultures were restimulated with peptide, rIL2 and irradiated (3000 rads) autologous or HLA-A2 matched feeder cells, and the cultured PBMC were tested for CTL activity on day 14. Selected cultures that displayed peptide specific cytolytic activity were expanded by weekly restimulation with $1 \times 10^6$ irradiated (6000 rads) allogeneic PBMC and $1 \times 10^5$ irradiated (18000 rads) JY cells (allogeneic EBV-B transformed cell line, HLA-A2.1, B7, Cw7) (14) in 1 ml of complete medium containing 1 µg/ml peptide, 20 U/ml IL2 and 1 µg/ml phytohemagglutinin (PHA) (Sigma, St. Louis, Mo.).

For cytotoxicity assays, target cells consisted either of a) autologous PHA stimulated blasts or allogeneic HLA matched and mismatched EBV-transformed B lymphoblastoid cell lines (B-LCL) incubated overnight with synthetic peptides at 10 µg/ml; b) stable B-LCL transfectants described above; or c) B-LCL infected with recombinant vaccinia viruses (described below). B-LCL were either purchased from The American Society for Histocompatibility and Immunogenetics (Boston, Mass.) or established from our own pool of patients and normal donors as described in copending application Ser. No. 07/935,898. The cells were maintained in RPMI 1640 supplemented with L-glutamine (2 mM), gentamicin (10 µg/ml), penicillin (50 U/ml), streptomycin (50 µg/ml), HEPES (5 mM), and 10% (vol/vol) heat inactivated FCS (Gibco, Grand Island, N.Y.). Short term lines of autologous PBMC blasts were produced by stimulating peripheral blood PBMC with PHA at 1 µg/ml in the RPMI 1640 supplemented with L-glutamine (2 mM), gentamicin (10 µg/ml), penicillin (50 U/ml), streptomycin (50 µg/ml), HEPES (5 mM), 10% (vol/vol) heat inactivated FCS, and 10 U/ml rIL2 for 7 days before use as target cells. Vaccinia infected targets were prepared by infection of $1 \times 10^6$ cells at 50 plaque-forming U/cell on a rocking plate at room temperature for one hour followed by a single wash and overnight incubation at 37° C.

Target cells were labeled with 100 µCi of $^{51}Cr$ (Amersham, Arlington Heights, Ill.) for one hour and washed three times with HBSS. Cytolytic activity was determined in a standard 4 hour $^{51}Cr$ release assay using U-bottom 96 well plates containing 5000 targets per well. All assays were performed in duplicate. Percent cytotoxicity was determined from the formula: 100×[(experimental release−spontaneous release)/(maximum release−spontaneous release)]. Maximum release was determined by lysis of targets by detergent (1% Triton X-100, Sigma). Spontaneous release was less than 25% of maximal release in all assays.

Two HLA-A2 positive patients with acute hepatitis (A-1 and A-3) wereinitially selected for analysis of the CTL response to HbsAg329-348 (ASARFSWLSLLVPFVQWFVG (SEQ ID NO:22)), which contains 2 overlapping HLA a2.1 allele specific binding motifs (WLSLLVPFV(SEQ ID NO:10) and LLVPFVQWFV(SEQ ID NO:25)). One of these patients (A-3) was known from previous experiments to display an HLA A2 restricted CTL response to a 10 residue HBV nucleocapsid epitope (HBcAg 18-27) that also represents an HLA A2.1 allele specific binding motif (FLPSDFFPSV(SEQ ID NO:23)). This patient was considered a potential responder to one or both of the motifs in HBsAg329-348. Another patient (A-1), known to be a nonresponder to HBsAg18-27, was studied for comparison.

HBsAg329-348 specific CTL lines were generated from PBMC of both patients by stimulation with the peptide as described above. After 2–3 weeds of stimulation, both patients displayed a strong cytotoxic response against a homozygous HLA A2.1 positive EBV cell line (JY) prepulsed with the HBsAg329-348 peptide. Patient A-1's HBsAg329-348 specific cell line was selected for cloning.

CTL lines were cloned originally at 1, 10, and 100 cells per well and then subcloned at 0.3 or 1 cell per well in 96 well microtiter plates. The cells were plated in the presence of peptide (1 µg/ml), PHA (1 µg/ml), rIL-2 (20 U/ml), irradiated (6000 rads) allogeneic PBMC ($10^5$ cells/well), and irradiated (18000 rads) JY cells ($10^4$ cells/well). HBV specific clones were restimulated in a 24 well plate as described above except that the peptide was omitted and irradiated JY cells, transfected with a plasmid that confers stable expression of the HBV large envelope antigen (EBO-preS1, reference 10), were added at $10^5$ cells per well.

Using patient A-1's HBsAg329-348 specific cell line four clones were derived from cells plated at 1 cell per well (clone B13, B16, B17) or 0.3 cells per well (clone B3). Clone B3 was tested against a panel of allogeneic target cells partially matched with the effectors at the level of HLA class I alleles. Using allogeneic target cells partially matched at HLA class I with patient A-1, the cytolytic activity of clone B3 was found to be HLA-A2 restricted, due to the presence of 2 HLA-A2.1 binding motifs in the peptide. An HBsAg329-348 specific polyclonal CTL line derived from patient A-3 was also determined to be HLA-A2 restricted in the same manner. Since the HLA-A2 subtypes of the patients were not determined, it is not known if the CTL response to the peptides is restricted only by the HLA-A2.1 allele or whether it extends to other HLA-A2 subtypes as well.

To determine a minimum, optimal HLA-A2 restricted CTL epitope within HBsAg329-348, a panel of amino-terminal truncations and overlapping nine-mers and ten-mers derived from the HBsAg329-348 sequence were produced to map the HLA-A2 restricted CTL epitope(s) present in this 20 residue peptide, which contains 2 overlapping ideal HLA-A2.1 binding motifs. The HLA-A2 restricted CTL clone B17 from patient A-1, and a polyclonal CTL line 1B9 from patient A-3, derived by repetitive stimulation of the initial cell line described above and HBsAg329-348, were used as effector cells to establish the fine specificity of the CTL response to HBsAg329-348. Target cells were produced by incubating an HLA-A2.1 positive B cell line (JY) either with the original 20-mer or with the truncated peptides.

Figure 1B:
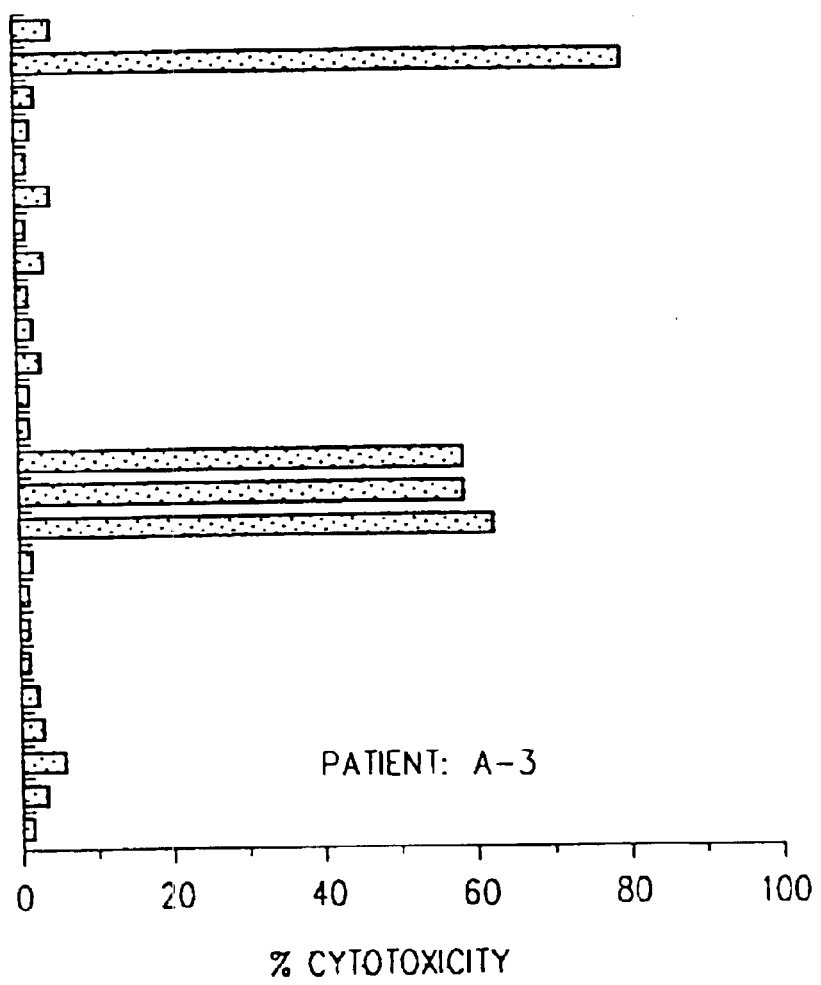

The results, shown in FIG. 1, indicated that only the first of the HLA-A2.1 binding motifs (HBsAg335-343)is recognized by the CTL. Furthermore, the data demonstrate that this peptide (WLSLLVPFV (SEQ ID NO:10)) is the minimal, optimal HLA-A2 restricted epitope recognized by HBsAg329-348 stimulated CTL, since omission of the extreme amino-terminal or the extreme carboxy-terminal residue from HBsAg335-343 abolishes recognition by the CTL.

Figure 2:
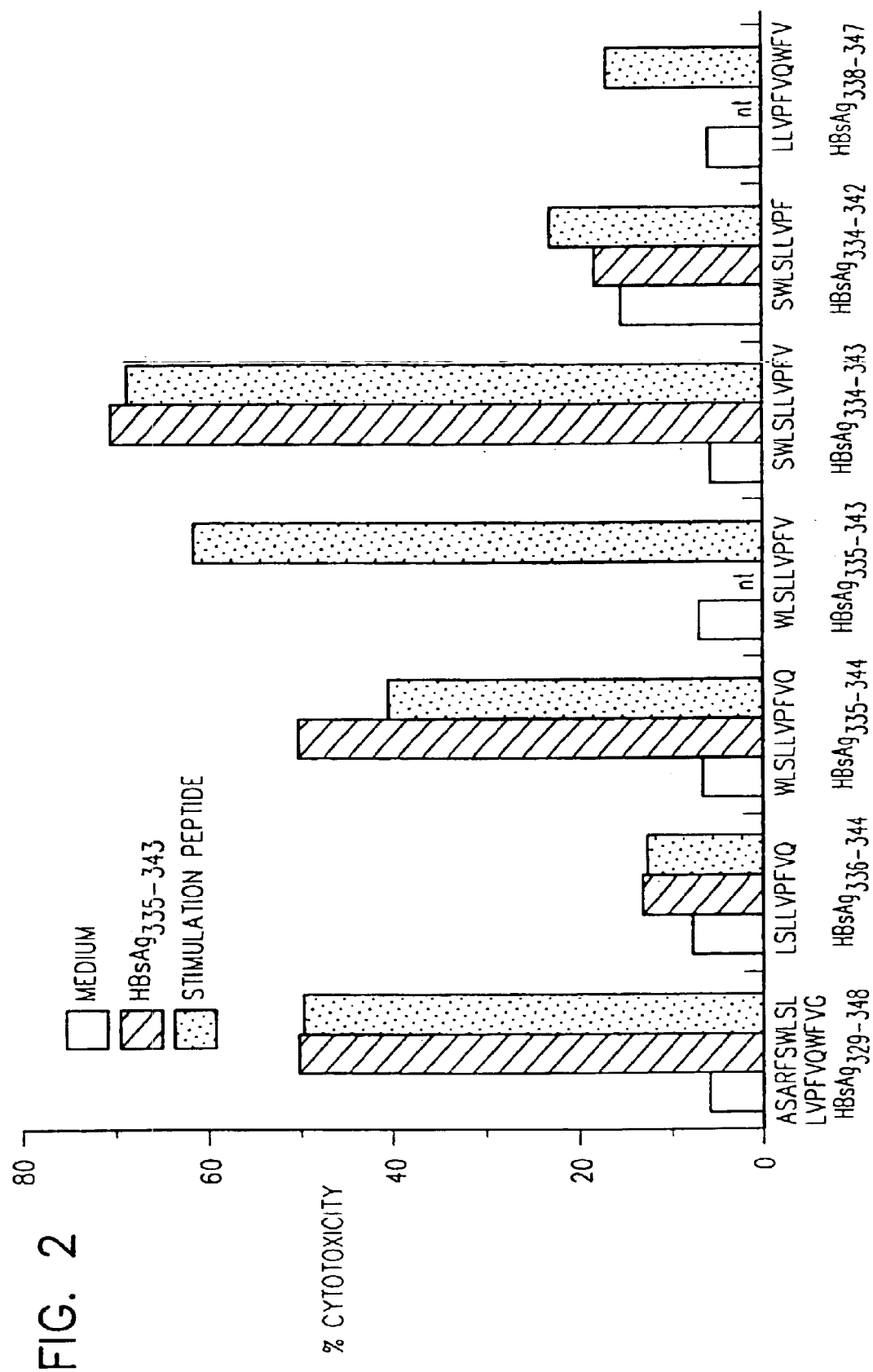
FIG. 2 further confirms that an optimal epitope within HBsAg329-348 for in vitro CTL indusction is HBsAg335-343 (SEQ ID NOS:22, 53, 52, 10, 51, 50 and 25, respectively).

The superiority of HBsAg335-343 at the effector level was reiterated when the peptides were used to stimulate a CTL response in PBMC from patient A-1. Synthetic peptides representing assorted HBsAg329-348 subunits were used at 10 µM to stimulate PBMC of patient A-1. After 2 weeks of stimulation the cytotoxicity of these lines was tested at E:T of 60:1 against JY target cells prepulsed with 10 µM of the same peptide and JY target cells prepulsed with 10 µM HBsAg335-343. Results shown in FIG. 2 represent % lysis in a 4 hour $^{51}Cr$ release assay. As can be seen in FIG. 2, although HBsAg335-343 and its extended variants proved capable of inducing a CTL response, omission of the extreme amino- and carboxy-terminal amino acids completely abolished the ability of the peptides to stimulate a CTL response, thereby reinforcing the conclusion that HBsAg335-343 is the minimal optimal HLA-A2 restricted epitope between residues 329-348 of HBsAg.

EXAMPLE II

CTL Response to Seven HLA-A2.1 Binding Motifs in HBVenv

Seven ideal HLA-A2.1 allele specific binding motifs, defined as peptides between 9–10 residues in length that contain a leucine in the second position and a valine as the carboxy-terminal residue, are present in the HBsAg region of the HBV envelope protein (Table III). Based on the results obtained in Example I, the ability of these seven envelope peptides, plus the known HLA-A2 restricted HBV nucleocapsid epitope (HBcAg18-27), to stimulate a CTL response in 12 HLA-A2 positive patients with acute hepatitis B, was examined. For comparison, six HLA-A2 positive patients with chronic hepatitis and 6 uninfected normal controls were tested for responsiveness to the same panel of peptides.

TABLE III

HBV-derived HLA-A2.1 binding motifs and peptides

|   | Peptide | Sequence | Seq. ID No. |
|---|---|---|---|
| 1 | HBcAg18-27 | FLPSDFFPSV | 23 |
| 2 | HBsAg201-210 | SLNFLGGTTV | 24 |
| 3 | HBsAg251-259 | LLCLIFLLV | 7 |
| 4 | HBsAg260-269 | LLDYQGMLPV | 9 |
| 5 | HBsAg335-343 | WLSLLVPFV | 10 |
| 6 | HBsAg338-347 | LLVPFVQWFV | 25 |
| 7 | HBsAg348-357 | GLSPTVWLSV | 26 |
| 8 | HBsAg378-387 | LLPIFFCLWV | 27 |

PBMC from acute patients (A-1 to A-12), chronic patients (C-1 to C-6), and normal subjects (N-1 to N-6) were stimulated with the following synthetic peptides: 1=HBcAg18-27, 2=HBsAg201-210, 3=HBsAg251-259, 4=HBsAg260-269, 5=HBcAg335-343, 6=HBsAg338-347, 7=HBsAg348-357, 8=HBsAg378-387, for two weeks as described in Example I, and tested in a 4 hour $^{51}$Cr release assay against JY target cells prepulsed overnight with the same peptide. Peptide specific cytotoxicity was measured by subtracting the $^{51}$Cr release by JY target cells not prepulsed with peptide from the $^{51}$Cr release by JY target cells prepulsed with the peptide. Results shown (FIG. 3) represent % specific lysis in a 4 hour $^{51}$Cr release assay.

Figure 3:
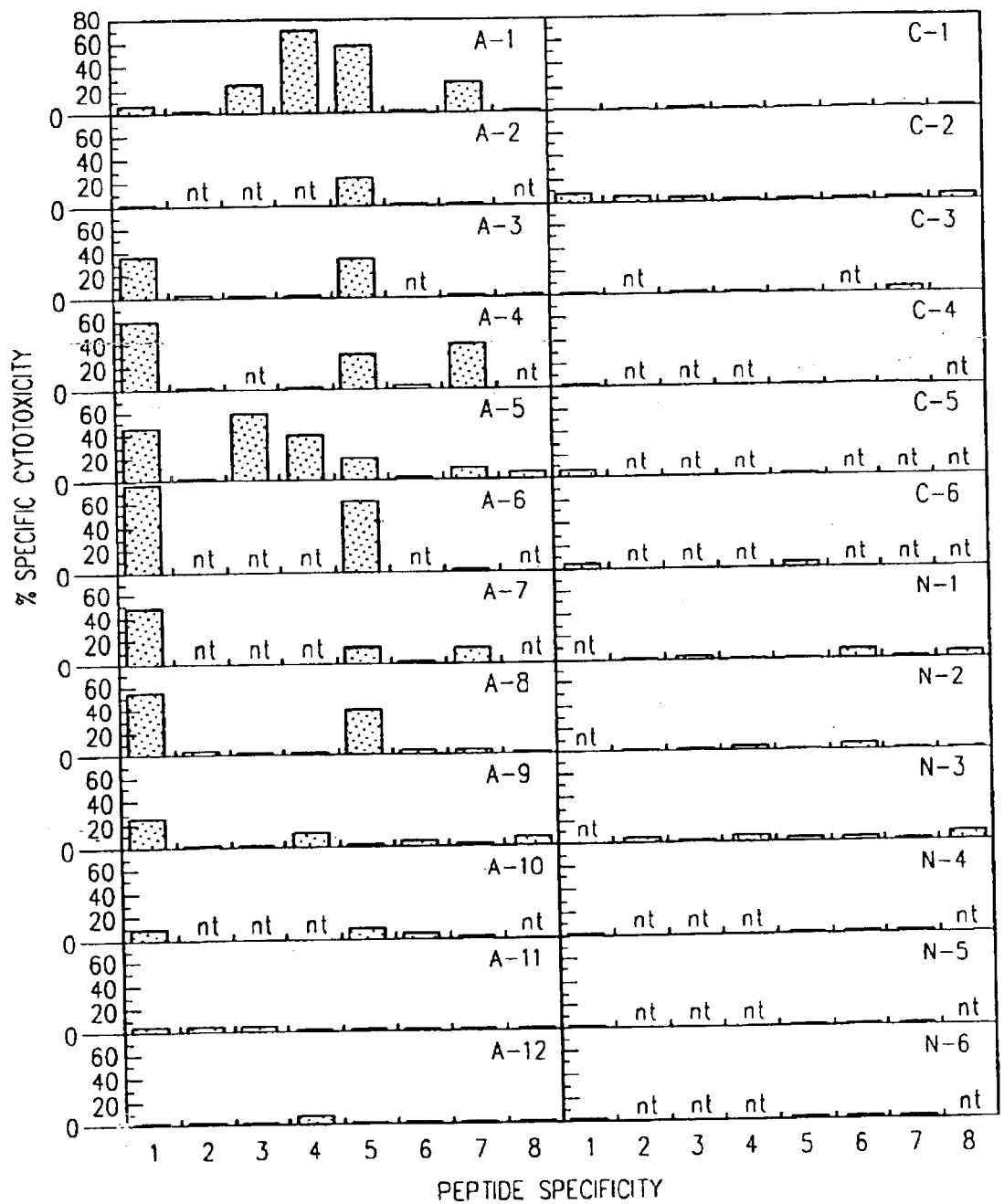
FIG. 3 shows the HBV specific CTL response in patients with acute hepatitis B infection, chronic hepatitis B infection, and normal subjects. PBMC from acute patients (A-1 to A-12), chronic patients (C-1 to C-6), and normal subjects (N-1 to N-6) were stimulated with the following synthetic peptides: 1-HBcAg18-27, 2=HBsAg201-210, 3=HBsAg251-259, 4=HBsAg260-269, 5-HBsAg335-343, 6=HBsAg338-347, 7=HBsAg348-357, 8=HBsAg378-387.

As can be seen in FIG. 3, nine of the twelve HLA-A2 positive patients with acute hepatitis responded to at least one of the peptides in the panel. In contrast, none of the six HLA-A2 positive uninfected normal controls responded to any of the peptides following the same in vitro stimulation strategy, suggesting that responsiveness to these peptides by the patients reflects in vivo priming by the corresponding HBV-derived epitopes.

Importantly, eight of the nine responders recognized multiple epitopes within the panel, indicating that the CTL response to HBV during acute hepatitis is both polyclonal and multispecific. Furthermore, there was substantial variation in the spectrum of epitopes recognized among the nine responders, with certain epitopes being recognized more frequently than others. For example, HBcAg18-27 and HBsAg335-343 were recognized individually by seven and eight of the nine responders, respectively, and when combined they were recognized by all nine of the responders. In contrast, HBsAg348-357, HBsAg251-259 and HBsAg260-269 were recognized by only 3/9, 2/5 and 3/6 of the responders in whom they were tested.

Nucleotide sequence analysis of circulating virion DNA in acutely infected patients showed that all patients, including the CTL nonresponders, were infected by viruses that expressed the precise amino acid sequence present in the prototype HBsAg335-343 peptide used to stimulate expansion of CTL in vitro. Since residues 335-343 are known to be conserved in all the published HBV sequences derived from all 4 HBV subtypes, as published in the GenBank-72 database, as well as in the 10 patients studied herein, it may be concluded that HBsAg335-343 is an HBV group specific CTL epitope. The same was not true for HBsAg348-357, however, since only seven of the ten patients were found to be infected by viruses that encode the prototype sequence used for in vitro stimulation (GLSPTVWLSV (SEQ ID NO:26)). The remaining three patients (A-9, A-10, A-13) displayed a variant sequence in which the carboxy-terminal valine was substituted by alanine at position 357. Among the patients infected by the prototype virus, CTL responders and nonresponders to HBsAg348-357 were observed, just as for the response to BsAg335-343. On the other hand, none of the 3 patients infected by the variant virus displayed a CTL response to the prototype peptide.

It is noteworthy that all nine responders subsequently became HBsAg negative and their liver disease completely resolved. In contrast, all six patients with chronic hepatitis, who failed to clear the virus, also failed to mount a peripheral blood CTL response to any of these epitopes. Three of the acutely infected patients (A-10, A-11, A-12) also failed to respond to any of these peptides. Furthermore, one of the nonresponders (A-11) developed chronic active hepatitis and was still HBsAg positive 13 months after his acute illness. These combined data strongly suggest a relationship between the CTL response and viral clearance. However, nonresponder patient A-12 seroconverted to HBsAg negativity between 1–4 months after disease onset.

As indicated in Table II and FIG. 3, four of the nine responders shared only the HLA A2 allele with the JY target cell line used in this study (HLA-A2, B7, Cw7), demonstrating that the response to all of the peptides was HLA-A2 restricted in these individuals. Since the remaining responders also share the HLA B7 and/or Cw7 alleles present in the JY target cells in addition to A2, it is possible, although unlikely, that these alleles could also serve as restriction elements for these epitopes in these patients.

The molecular basis for the differential immunogenicity of the seven HBV envelope peptides was not immediately evident from a comparison of their sequences. Potential differences in the relative binding affinity of the peptides to HLA-A2.1 were examined by determining the ability of the seven envelope peptides to compete with the binding of an unrelated HLA-A2 restricted nucleocapsid epitope (HBcAg18-27) to a homozygous HLA-A2.1 positive B cell line (JY).

The competitive binding inhibition assay used an HBcAg18-27 specific CTL clone from patient A-4 as a source of effector cells. Blocking peptides (1, 10, 100 µM) were added to a mixture of $^{51}$Cr-labelled, HLA-A2.1 positive JY target cells and effector cells (E:T=40:1, 3000 target cells/well) for 40 minutes before the addition of a subsaturating concentration (0.03 µM) of the target peptide, HBcAg$^{18-27}$. The binding ability of each peptide was assessed by calculating the degree to which it blocked the lysis of target cells in a 4 hour $^{51}$Cr release assay.

Figure 4:
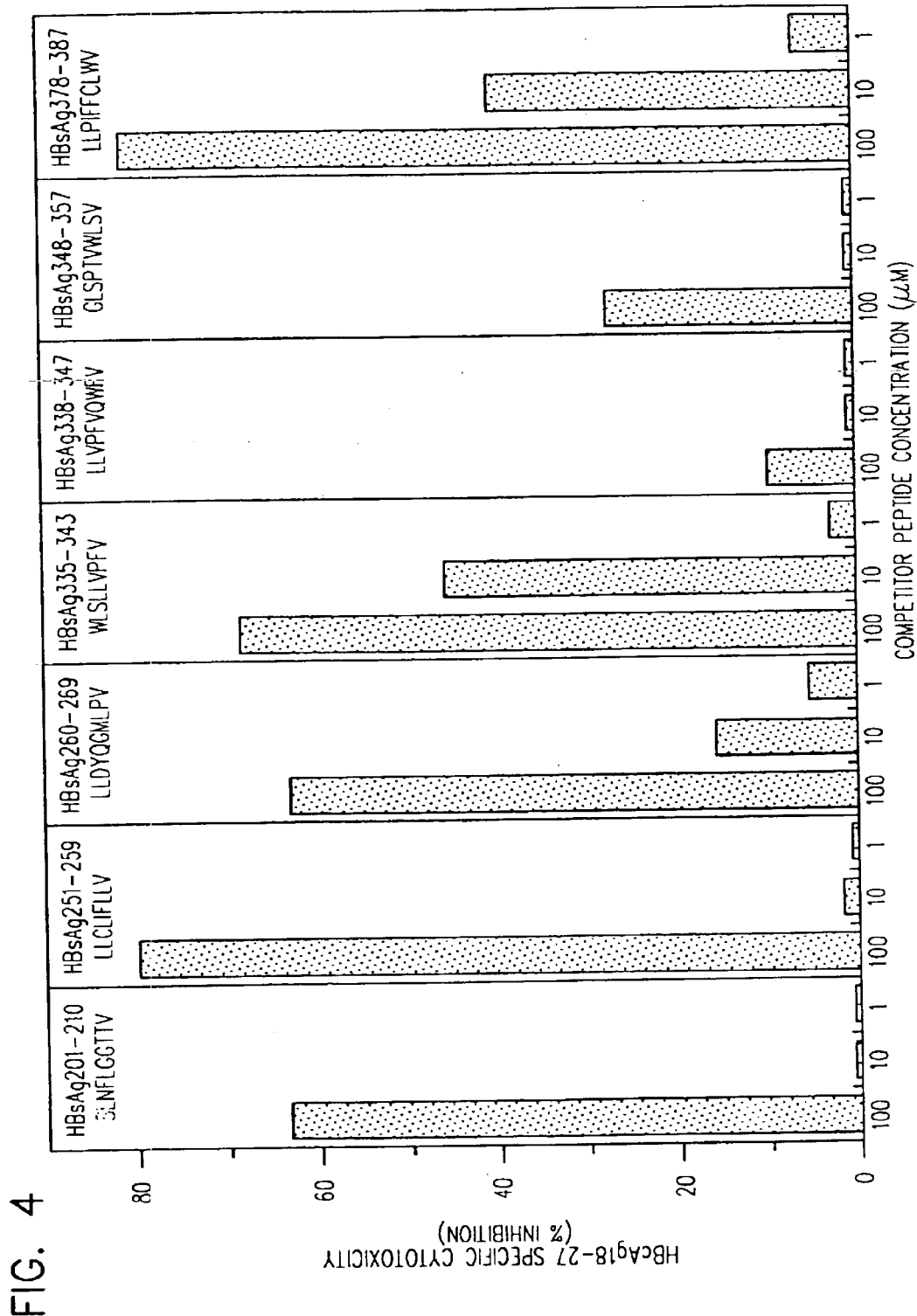
FIG. 4 shows the results of HLA-A2.1 competitive binding inhibition assays (SEQ ID NOS:24, 7, 9, 10, 25, 26 and 27, respectively), represented as % inhibition of NBcAg18-27 specific lysis in a 4 hour $^{51}$Cr release assay.

As shown in FIG. 4, all four immunogenic peptides and two of the three nonimmunogenic peptides bound to the HLA-A2.1 molecule, but with widely (more than 100-fold) variable efficiencies that did not correlate with their relative immunogenicity. Importantly, the only peptide that did not bind to HLA-A2.1 in this assay (HBsAg337-348) was nonimmunogenic. For the other two nonimmunogenic peptides, however, the HLA-A2.1 binding affinity was as high or higher than some of the immunogenic peptides. Thus, although the capacity of a peptide to bind to this class I molecule is required for immunogenicity, it does not guarantee it. This suggests that the additional factors at the level of antigen processing and the T cell repertoire may play a role in determining which HLA-A2.1 binding peptides within a viral protein are able to induce a CTL response.

EXAMPLE III

Peptide Specific CTL Recognize Endogenous HBenv Antigen

The ability of $HBsAg_{335-343}$ and $HBsAg_{348-357}$ specific CTL to recognize endogenously synthesized antigen was examined by measuring their ability to lyse target cells that had been infected with two groups of recombinant vaccinia viruses which encode the large, middle and major envelope polypeptides derived from cloned HBV genomes of either the ayw or the adw subtypes of HBV.

Recombinant vaccinia viruses expressing the HBV large, middle and major envelope polypeptides (adw subtype) and a corresponding control wild type vaccinia were obtained (Smith et al., *Nature* 302:490 (1983); Cheng et al., *J. Virol.* 60:337 (1986); and Cheng and Moss, *J. Virol.* 61:1286 (1987), each of which are incorporated herein by reference). An independent series of recombinant vaccinia viruses expressing the same three HBV envelope polypeptides of the HBV ayw subtype was derived as follows. For expression of the HBsAg, an XhoI/SphI restriction fragment containing nucleotides 1409–2514 of the HBV sequence was cloned into a vaccinia virus expression vector downstream from the 7.5 K early/late promoter. For the preS1 expressing vaccinia virus, a Bgl II/Sph I fragment containing nucleotides 937–2514 was used. For cloning the preS2 coding sequence, first a short adapter oligonucleotide was synthesized which started at nucleotide 1267 (e.g., six base-paris upstream from the preS2 start codon) and spanned the Eco RI site at position 1280. After cloning this oligonucleotide into the vaccinia virus expression vector, the coding sequence was completed by recloning the Eco RI/SphI HBV fragment (nucleotides 1280–2514) into this intermediate construct. Generation of recombinant vaccinia viruses was done according to standard procedures as described in Smith et al., supra. Stable transfectants that expressed the HBV envelope proteins (ayw subtype) were produced by transfection of B-LCL with a panel of EBV based expression vectors that contain the corresponding HBV (ayw subtype) coding regions, as described in Guilhot et al., *J. Virol.* 66:2670 (1992), incorporated herein by reference.

An $HBsAg_{335-343}$ specific CTL line (patient A-1) and an $HBsAg_{348-357}$ specific CTL line (patient A-4) were generated by stimulation with peptide sequences WLSLLVPFV (SEQ ID NO:10) and GLSPTVWLSV (SEQ ID NO:26), respectively. CTL were incubated with $^{5}$Cr-labelled JY target cells that had been preincubated either with media, with the inducing peptide or (in the case of $HBsAg_{348-357}$) with a variant peptide (GLSPTVWLSA (SEQ ID NO:57)). CTL were also incubated with $^{51}$Cr-labelled JY target cells that had been infected with a panel of 6 recombinant vaccinia viruses that express the HBV major (V-HBs), middle (V-preS2), and large (V-preS1) envelope polypeptides derived from ayw and adw HBV genomes. Wild-type vaccinia viruses (V-wt) were used as controls. The $HBsAg_{335-343}$ specific CTL line (right panel) was used at an E:T=40:1. The $HBsAg_{348-357}$ specific CTL line (left panel) was used at an E:T=3:1. Results shown represent % lysis in a 4 hour $^{51}$Cr release assay.

Figure 5:
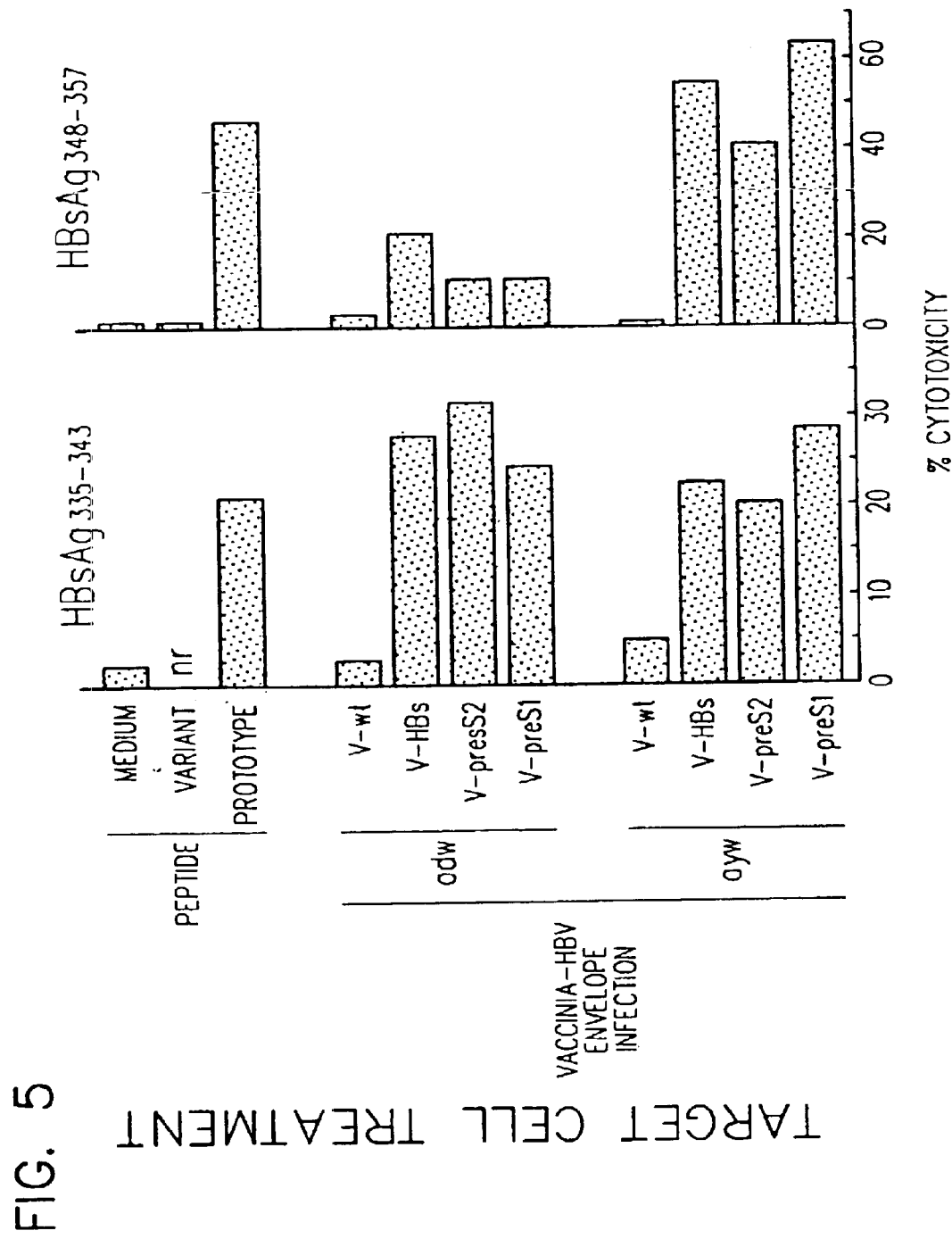
FIG. 5 illustrates that the CTL response to HBsAg335-343 and HBsAg348-357 are group specific and subtype specific, respectively, and that the synthetic peptides contain epitopes that are also generated by the endogenous processing of the large, middle and major HBV envelope polypeptides within infected cells.

Both $HBsAg_{335-343}$ and $HBsAg_{348-357}$ specific CTL from patients A-1 and A-4 were able to lyse recombinant vaccinia virus infected target cells that synthesize all three of the HBV envelope proteins (FIG. 5). This indicates that both of these synthetic peptides represent epitopes that are generated by the endogenous processing of the large, middle and major HBV envelope polypeptides within infected cells.

Importantly, $HBsAg_{335-343}$ specific CTL could lyse targets that were infected by both sets of recombinant vaccinia viruses with equal efficiency, with the $HBsAg_{348-357}$ specific CTL lysed with ayw infected target cell panel much more efficiently than the adw targets.

The results described in the foregoing Examples illustrate that the CTL response to HBV in man appears to be quite polyvalent, presumably to afford more efficient protection against this serious viral infection. Furthermore the data indicate that the peptide stimulation strategy employed herein is both efficient and effective for the identification and analysis of the polyvalent response, restricted as it is by the polymorphic HLA class I locus. As additional HLA allele specific binding motifs are identified, HBV-derived peptides containing these motifs can be used for in vitro stimulation of CTL precursors.

All publications, patents and patent applications mentioned in this specification are herein incorporated by reference into the specification to the same extent as if each individual publication, patent or patent application was specifically and individually indicated to be incorporated herein by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An expression vector comprising a nucleic acid that encodes an immunogenic peptide of 50 amino acids or less in length wherein said peptide comprises at least seven contiguous amino acids of an amino acid sequence selected from the group consisting of $HBenv_{248-257}$, $HBenv_{249-257}$, $HBenv_{249-258}$, $HBenv_{250-258}$, $HBenv_{251-259}$, and $HBenv_{251-260}$, and wherein said peptide, or a fragment thereof, binds to an appropriate HLA molecule to form a complex recognized by cytotoxic T cells which T cells recognize a native HBV antigen.

2. The expression vector of claim 1, wherein the peptide is 25 amino acids or less in length.

3. The expression vector of claim 2, wherein the peptide is 8, 9, 10, or 11 amino acids in length.

4. The expression vector of claim 1, wherein the nucleic acid encodes the peptide and at least one additional immunogenic peptide.

5. The expression vector of claim 4, wherein the additional immunogenic peptide elicits a T-helper cell-mediated immune response.

6. The expression vector of claim 4, wherein the additional immunogenic peptide elicits a cytotoxic T lymphocyte response.

7. An expression vector comprising a nucleic acid that encodes an immunogenic peptide consisting of the amino acid sequence that is $HBenv_{348-357}$.

8. The expression vector of claim 7, wherein the nucleic acid encodes the peptide and at least one additional immunogenic peptide.

9. The expression vector of claim 8, wherein the additional immunogenic peptide elicits a T-helper cell-mediated immune response.

10. The expression vector of claim 8, wherein the additional immunogenic peptide elicits a cytotoxic T lymphocyte response.

11. A method of stimulating a cytotoxic T cell response, said method comprising administering an expression vector comprising a nucleic acid that encodes a peptide of 50 amino acids or less in length wherein said peptide comprises at least seven contiguous amino acids of an amino acid sequence selected from the group consisting of $HBenv_{248-257}$, $HBenv_{249-257}$, $HBenv_{249-258}$, $HBenv_{250-258}$, $HBenv_{251-259}$, and $HBenv_{251-260}$, and wherein said neptide, or a fragment thereof, binds to an appropriate HLA molecule to form a complex recognized by cytotoxic T cells which T cells recognize a native HBV antigen.

12. A method of stimulating a cytotoxic T cell response, said method comprising administering an expression vector comprising a nucleic acid that encodes a peptide consisting of the amino acid sequence that is $HBenv_{348-357}$.

* * * * *

UNITED STATES PATENT AND TRADEMARK OFFICE
CERTIFICATE OF CORRECTION

PATENT NO. : 6,919,203 B2
DATED : July 19, 2005
INVENTOR(S) : Francis V. Chisari It is certified that error appears in the above-identified patent and that said Letters Patent is hereby corrected as shown below:

Column 4,
Lines 8-9, "NBcAg18-27" should read -- HBcAg18-27 --.

Column 12,
Line 30, "*Cloning. A Laboratory*" should read -- Cloning, A Laboratory --.

Column 20,
Line 43, "(HBsAg335-343)is" should read -- (HBsAg335-343) is --.

Column 22,
Line 18, "to BsAg335-343." should read -- to HBsAg335-343. --.

Column 24,
Line 5, "with $^5$Cr-labelled JY" should read -- with $^{51}$Cr-labelled JY --.

Column 50,
Line 3, "wherein said neptide" should read -- wherein said peptide --.

Signed and Sealed this

Twenty-eighth Day of February, 2006

JON W. DUDAS
*Director of the United States Patent and Trademark Office*

SEQUENCE LISTING (1) GENERAL INFORMATION:

(iii) NUMBER OF SEQUENCES: 57

(2) INFORMATION FOR SEQ ID NO: 1:

(i) SEQUENCE CHARACTERISTICS:

(A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 1:

Phe Leu Leu Thr Arg Ile Leu Thr Ile
1               5

(2) INFORMATION FOR SEQ ID NO: 2:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

Phe Ile Leu Leu Leu Cys Leu Ile Phe Leu Leu Val Leu
1               5                   10

(2) INFORMATION FOR SEQ ID NO: 3:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

Phe Ile Leu Leu Leu Cys Leu Ile Phe Leu
1               5                   10

(2) INFORMATION FOR SEQ ID NO: 4:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

Ile Leu Leu Leu Cys Leu Ile Phe Leu
1               5

(2) INFORMATION FOR SEQ ID NO: 5:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

Ile Leu Leu Leu Cys Leu Ile Phe Leu Leu
1               5                   10

(2) INFORMATION FOR SEQ ID NO: 6:

```
    (i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

Leu Leu Leu Cys Leu Ile Phe Leu Leu
1               5

(2) INFORMATION FOR SEQ ID NO: 7:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 7:

Leu Leu Cys Leu Ile Phe Leu Leu Val
1               5

(2) INFORMATION FOR SEQ ID NO: 8:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 8:

Leu Leu Leu Cys Leu Ile Phe Leu Leu Val Leu
1               5                   10

(2) INFORMATION FOR SEQ ID NO: 9:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

Leu Leu Asp Tyr Gln Gly Met Leu Pro Val
1               5                   10

(2) INFORMATION FOR SEQ ID NO: 10:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 10:

Trp Leu Ser Leu Leu Val Pro Phe Val
1               5

(2) INFORMATION FOR SEQ ID NO: 11:
```

(i) SEQUENCE CHARACTERISTICS:
    (A) LENGTH: 10 amino acids
    (B) TYPE: amino acid
    (C) STRANDEDNESS: <Unknown>
    (D) TOPOLOGY: linear (ii) MOLECULE TYPE: peptide (xi) SEQUENCE DESCRIPTION: SEQ ID NO: 11:

Ser Ile Leu Ser Lys Thr Gly Asp Pro Val
 1               5                  10

(2) INFORMATION FOR SEQ ID NO: 12:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 12:

Val Leu Gln Ala Gly Phe Phe Leu Leu
 1               5

(2) INFORMATION FOR SEQ ID NO: 13:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 13:

Phe Leu Gly Gly Thr Pro Val Cys Leu
 1               5

(2) INFORMATION FOR SEQ ID NO: 14:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 14:

Ser Ile Val Ser Pro Phe Ile Pro Leu Leu
 1               5                  10

(2) INFORMATION FOR SEQ ID NO: 15:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 15:

Ser Trp Leu Ser Leu Leu Val Pro Phe Val
 1               5                  10

(2) INFORMATION FOR SEQ ID NO: 16:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 16:

Trp Leu Ser Leu Leu Val Pro Phe Val Gln
1               5                   10

(2) INFORMATION FOR SEQ ID NO: 17:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 17:

Met Asp Ile Asp Pro Tyr Lys Glu Phe Gly Ala Thr Val Glu Leu
1               5                   10                  15

Ser Phe Leu Pro
            20

(2) INFORMATION FOR SEQ ID NO: 18:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 18:

Pro His His Tyr Ala Leu Arg Gln Ala Ile Leu Cys Trp Gly Glu Leu
1               5                   10                  15

Met Tyr Leu Ala
            20

(2) INFORMATION FOR SEQ ID NO: 19:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 19:

Leu Leu Trp Phe His Ile Ser Cys Leu Thr Phe Gly Arg Glu Thr Val
1               5                   10                  15

Ile Glu Tyr Leu
            20

(2) INFORMATION FOR SEQ ID NO: 20:

(i) SEQUENCE CHARACTERISTICS:
        (A) LENGTH: 15 amino acids
        (B) TYPE: amino acid
        (C) STRANDEDNESS: <Unknown>

(D) TOPOLOGY: linear (ii) MOLECULE TYPE: peptide (xi) SEQUENCE DESCRIPTION: SEQ ID NO: 20:

Glu Tyr Leu Val Ser Phe Gly Val Trp Ile Arg Thr Pro Pro Ala
1               5                  10                  15

(2) INFORMATION FOR SEQ ID NO: 21:

(i) SEQUENCE CHARACTERISTICS:
            (A) LENGTH: 20 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 21:

Val Ser Phe Gly Val Trp Ile Arg Thr Pro Pro Ala Tyr Arg Pro Pro
1               5                  10                  15

Asn Ala Pro Ile
            20

(2) INFORMATION FOR SEQ ID NO: 22:

(i) SEQUENCE CHARACTERISTICS:
            (A) LENGTH: 20 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 22:

Ala Ser Ala Arg Phe Ser Trp Leu Ser Leu Leu Val Pro Phe Val Gln
1               5                  10                  15

Trp Phe Val Gly
            20

(2) INFORMATION FOR SEQ ID NO: 23:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 23:

Phe Leu Pro Ser Asp Phe Phe Pro Ser Val
1               5                  10

(2) INFORMATION FOR SEQ ID NO: 24:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 24:

Ser Leu Asn Phe Leu Gly Gly Thr Thr Val
1               5                  10

(2) INFORMATION FOR SEQ ID NO: 25:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 25:

```
Leu Leu Val Pro Phe Val Gln Trp Phe Val
1               5                   10
```

(2) INFORMATION FOR SEQ ID NO: 26:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 26:

```
Gly Leu Ser Pro Thr Val Trp Leu Ser Val
1               5                   10
```

(2) INFORMATION FOR SEQ ID NO: 27:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 27:

```
Leu Leu Pro Ile Phe Phe Cys Leu Trp Val
1               5                   10
```

(2) INFORMATION FOR SEQ ID NO: 28:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 28:

```
Ser Ala Arg Phe Ser Trp Leu Ser Leu Leu Val Pro Phe Val Gln Trp
1               5                   10                  15

Phe Val Gly
```

(2) INFORMATION FOR SEQ ID NO: 29:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 29:

```
Ala Arg Phe Ser Trp Leu Ser Leu Leu Val Pro Phe Val Gln Trp Phe
1               5                   10                  15
Val Gly
```

(2) INFORMATION FOR SEQ ID NO: 30:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 30:

```
Arg Phe Ser Trp Leu Ser Leu Leu Val Pro Phe Val Gln Trp Phe Val
1               5                   10                  15
Gly
```

(2) INFORMATION FOR SEQ ID NO: 31:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 31:

```
Phe Ser Trp Leu Ser Leu Leu Val Pro Phe Val Gln Trp Phe Val Gl
1               5                   10                  15
```

(2) INFORMATION FOR SEQ ID NO: 32:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 32:

```
Ser Trp Leu Ser Leu Leu Val Pro Phe Val Gln Trp Phe Val Gly
1               5                   10                  15
```

(2) INFORMATION FOR SEQ ID NO: 33:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 33:

```
Trp Leu Ser Leu Leu Val Pro Phe Val Gln Trp Phe Val Gly
1               5                   10
```

(2) INFORMATION FOR SEQ ID NO: 34:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 34:

Leu Ser Leu Leu Val Pro Phe Val Gln Trp Phe Val Gly
1               5                  10

(2) INFORMATION FOR SEQ ID NO: 35:

(i) SEQUENCE CHARACTERISTICS:
            (A) LENGTH: 12 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 35:

Ser Leu Leu Val Pro Phe Val Gln Trp Phe Val Gly
1               5                  10

(2) INFORMATION FOR SEQ ID NO: 36:

(i) SEQUENCE CHARACTERISTICS:
            (A) LENGTH: 11 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 36:

Leu Leu Val Pro Phe Val Gln Trp Phe Val Gly
1               5                  10

(2) INFORMATION FOR SEQ ID NO: 37:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 37:

Leu Val Pro Phe Val Gln Trp Phe Val Gly
1               5                  10

(2) INFORMATION FOR SEQ ID NO: 38:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 38:

Val Pro Phe Val Gln Trp Phe Val Gly
1               5

(2) INFORMATION FOR SEQ ID NO: 39:

(i) SEQUENCE CHARACTERISTICS:
            (A) LENGTH: 8 amino acids
            (B) TYPE: amino acid
            (C) STRANDEDNESS: <Unknown>

```
        (D) TOPOLOGY: linear (ii) MOLECULE TYPE: peptide (xi) SEQUENCE DESCRIPTION: SEQ ID NO: 39:

Pro Phe Val Gln Trp Phe Val Gly
1               5

(2) INFORMATION FOR SEQ ID NO: 40:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 40:

Ala Ser Ala Arg Phe Ser Trp Leu Ser
1               5

(2) INFORMATION FOR SEQ ID NO: 41:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 41:

Ala Ser Ala Arg Phe Ser Trp Leu Ser Leu
1               5                   10

(2) INFORMATION FOR SEQ ID NO: 42:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 42:

Ser Ala Arg Phe Ser Trp Leu Ser Leu
1               5

(2) INFORMATION FOR SEQ ID NO: 43:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 43:

Ser Ala Arg Phe Ser Trp Leu Ser Leu Leu
1               5                   10

(2) INFORMATION FOR SEQ ID NO: 44:

(i) SEQUENCE CHARACTERISTICS:
        (A) LENGTH: 9 amino acids
        (B) TYPE: amino acid
```

```
            (C) STRANDEDNESS: <Unknown>
            (D) TOPOLOGY: linear (ii) MOLECULE TYPE: peptide (xi) SEQUENCE DESCRIPTION: SEQ ID NO: 44:

Ala Arg Phe Ser Trp Leu Ser Leu Leu
1               5

(2) INFORMATION FOR SEQ ID NO: 45:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 45:

Ala Arg Phe Ser Trp Leu Ser Leu Leu Val
1               5                   10

(2) INFORMATION FOR SEQ ID NO: 46:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 46:

Arg Phe Ser Trp Leu Ser Leu Leu Val
1               5

(2) INFORMATION FOR SEQ ID NO: 47:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 47:

Arg Phe Ser Trp Leu Ser Leu Leu Val Pro
1               5                   10

(2) INFORMATION FOR SEQ ID NO: 48:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 48:

Phe Ser Trp Leu Ser Leu Leu Val Pro
1               5

(2) INFORMATION FOR SEQ ID NO: 49:

(i) SEQUENCE CHARACTERISTICS:
            (A) LENGTH: 10 amino acids
```

(B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 49:

Phe Ser Trp Leu Ser Leu Leu Val Pro Phe
1               5                   10

(2) INFORMATION FOR SEQ ID NO: 50:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 50:

Ser Trp Leu Ser Leu Leu Val Pro Phe
1               5

(2) INFORMATION FOR SEQ ID NO: 51:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 51:

Leu Ser Leu Leu Val Pro Phe Val Gln
1               5

(2) INFORMATION FOR SEQ ID NO: 52:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 52:

Leu Ser Leu Leu Val Pro Phe Val Gln Trp
1               5                   10

(2) INFORMATION FOR SEQ ID NO: 53:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 53:

Ser Leu Leu Val Pro Phe Val Gln Trp
1               5

(2) INFORMATION FOR SEQ ID NO: 54:

(i) SEQUENCE CHARACTERISTICS:

```
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 54:

Ser Leu Leu Val Pro Phe Val Gln Trp Phe
1               5                   10

(2) INFORMATION FOR SEQ ID NO: 55:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 55:

Leu Leu Val Pro Phe Val Gln Trp Phe
1               5

(2) INFORMATION FOR SEQ ID NO: 56:

(i) SEQUENCE CHARACTERISTICS:
            (A) LENGTH: 9 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 56:

Leu Val Pro Phe Val Gln Trp Phe Val
1               5

(2) INFORMATION FOR SEQ ID NO: 57:

(i) SEQUENCE CHARACTERISTICS:
            (A) LENGTH: 10 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 57:

Gly Leu Ser Pro Thr Val Trp Leu Ser Ala
1               5                   10
```